United States Patent
Tahara et al.

(10) Patent No.: US 12,295,731 B2
(45) Date of Patent: May 13, 2025

(54) DRIVER AVAILABILITY DETECTION DEVICE AND DRIVER AVAILABILITY DETECTION METHOD

(71) Applicant: Mitsubishi Electric Corporation, Tokyo (JP)

(72) Inventors: Natsuki Tahara, Tokyo (JP); Genta Yoshimura, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 556 days.

(21) Appl. No.: 17/760,957

(22) PCT Filed: Oct. 4, 2019

(86) PCT No.: PCT/JP2019/039305
§ 371 (c)(1),
(2) Date: Mar. 16, 2022

(87) PCT Pub. No.: WO2021/064985
PCT Pub. Date: Apr. 8, 2021

(65) Prior Publication Data
US 2022/0346684 A1 Nov. 3, 2022

(51) Int. Cl.
*A61B 5/18* (2006.01)
*A61B 5/00* (2006.01)
(Continued)

(52) U.S. Cl.
CPC .............. *A61B 5/18* (2013.01); *A61B 5/6893* (2013.01); *A61B 5/7267* (2013.01); *G06V 20/597* (2022.01); *G06V 40/166* (2022.01)

(58) Field of Classification Search
CPC ....... A61B 5/18; A61B 5/6893; A61B 5/7267; G06V 20/597; G06V 40/166
See application file for complete search history.

(56) References Cited

U.S. PATENT DOCUMENTS 7,630,804 B2 * 12/2009 Aoki .................... G06V 40/103
340/576
9,714,037 B2 * 7/2017 DeRuyck ............. G06V 20/597
(Continued)

FOREIGN PATENT DOCUMENTS

JP         2008-35964 A      2/2008
JP         2008-204056 A     9/2008
(Continued)

OTHER PUBLICATIONS

International Search Report for PCT/JP2019/039305 dated Dec. 10, 2019 (PCT/ISA/210).
(Continued)

*Primary Examiner* — Gertrude Arthur Jeanglaude
(74) *Attorney, Agent, or Firm* — Sughrue Mion, PLLC

(57) ABSTRACT

A driver availability detection device includes an information acquisition unit to acquire information related to an occupant and a threshold setting unit to set an abnormal-state determination threshold for estimating the abnormal state of the occupant on a basis of an abnormal state score obtained by inputting the information related to the occupant acquired by the information acquisition unit to a machine learning model within a first threshold setting time.

11 Claims, 15 Drawing Sheets

(51) Int. Cl.
    *G06V 20/59*      (2022.01)
    *G06V 40/16*      (2022.01)

(56) References Cited

U.S. PATENT DOCUMENTS

| | | | |
|---|---|---|---|
| 11,345,234 B2* | 5/2022 | Kim | A61B 5/18 |
| 2003/0209893 A1* | 11/2003 | Breed | B60N 2/853 |
| | | | 701/45 |
| 2015/0314681 A1 | 11/2015 | Riley, Sr. et al. | |
| 2016/0262683 A1 | 9/2016 | Nakano et al. | |
| 2020/0074197 A1* | 3/2020 | Upmanue | B60K 35/60 |
| 2021/0016805 A1 | 1/2021 | Oba et al. | |

FOREIGN PATENT DOCUMENTS

| | | |
|---|---|---|
| JP | 2010-128649 A | 6/2010 |
| JP | 2010-134490 A | 6/2010 |
| JP | 2016-165349 A | 9/2016 |
| JP | 2018-61580 A | 4/2018 |
| JP | 2018-171124 A | 11/2018 |
| WO | 2019/188398 A1 | 10/2019 |

OTHER PUBLICATIONS

Notice of Reasons for Refusal dated Dec. 12, 2023 in Japanese Application No. 2021-550920.
Office Action dated Sep. 6, 2022 from the Japanese Patent Office in JP Application No. 2021-550920.

* cited by examiner

DRIVER AVAILABILITY DETECTION DEVICE AND DRIVER AVAILABILITY DETECTION METHOD

CROSS REFERENCE TO RELATED APPLICATIONS

This application is a National Stage of International Application No. PCT/JP2019/039305 filed Oct. 4, 2019.

TECHNICAL FIELD

The present invention relates to a driver availability detection device and a driver availability detection method for estimating an abnormal state oral occupant in a vehicle.

BACKGROUND ART

Conventionally, there has been known a technique that estimates whether or not an occupant of a vehicle is in an abnormal slate on the basis of information related to the occupant and a machine-learned model (hereinafter, referred to as "machine learning model").

At this time, in order to prevent the abnormal state of the occupant from being erroneously estimated, it is required to consider individual differences in information related to the occupant.

Here, for example, Patent Literature 1 discloses a technique of calculating, as an amount of biological variations, a difference between an average value of biological signals of a user who uses a vehicle for each time period and a biological signal of the user under measurement, and determining that the user is in poor physical condition in a case where the calculated amount of biological variations exceeds a predetermined poor condition threshold.

CITATION LIST

Patent Literatures

Patent Literature 1: JP2018-61580A

SUMMARY OF INVENTION

Technical Problem

As described above, in the conventional technique as disclosed in Patent Literature 1, in a case where an amount of biological variations of a user exceeds a poor condition threshold, it is determined that the user is in poor physical condition. This poor condition threshold is a fixedly determined range. However, the range of the biological information in which the physical condition of the user is good is different for each user. Consequently, even in a case where the amount of biological variations of the user exceeds the poor condition threshold, it does not necessarily mean that the user is actually in poor physical condition.

As a result, even if the conventional technique as disclosed in Patent Literature 1 is applied to a technique of estimating an abnormal state of an occupant of a vehicle on the basis of information related to the occupant and a machine learning model, there is still a problem that the abnormal state of the occupant may be erroneously estimated.

The present invention has been made to solve the above problem, and an object of the present invention is to provide a driver availability detection device that estimates an abnormal state of an occupant of a vehicle on the basis of information related to the occupant and a machine learning model, the driver availability detection device being capable of preventing erroneous estimation of the abnormal state of the occupant when estimating whether or not the occupant is man abnormal state.

Solution to Problem

A driver availability detection device according to the present invention estimates an abnormal state of an occupant of a vehicle on a basis of information related to the occupant of the vehicle and a machine learning model, and includes processing circuitry to acquire information related to the occupant and to set an abnormal-state determination threshold for estimating the abnormal state of the occupant on a basis of an abnormal state score obtained by inputting information related to the occupant to the machine learning model within a first threshold setting time.

Advantageous Effects of Invention

According to the present invention, in the driver availability detection device that estimates the abnormal state of the occupant of the vehicle on the basis of the information related to the occupant and the machine learning model, it is possible to prevent erroneous estimation of the abnormal state of the occupant when estimating whether or not the occupant is in the abnormal state.

DESCRIPTION OF EMBODIMENTS

Figure 1:
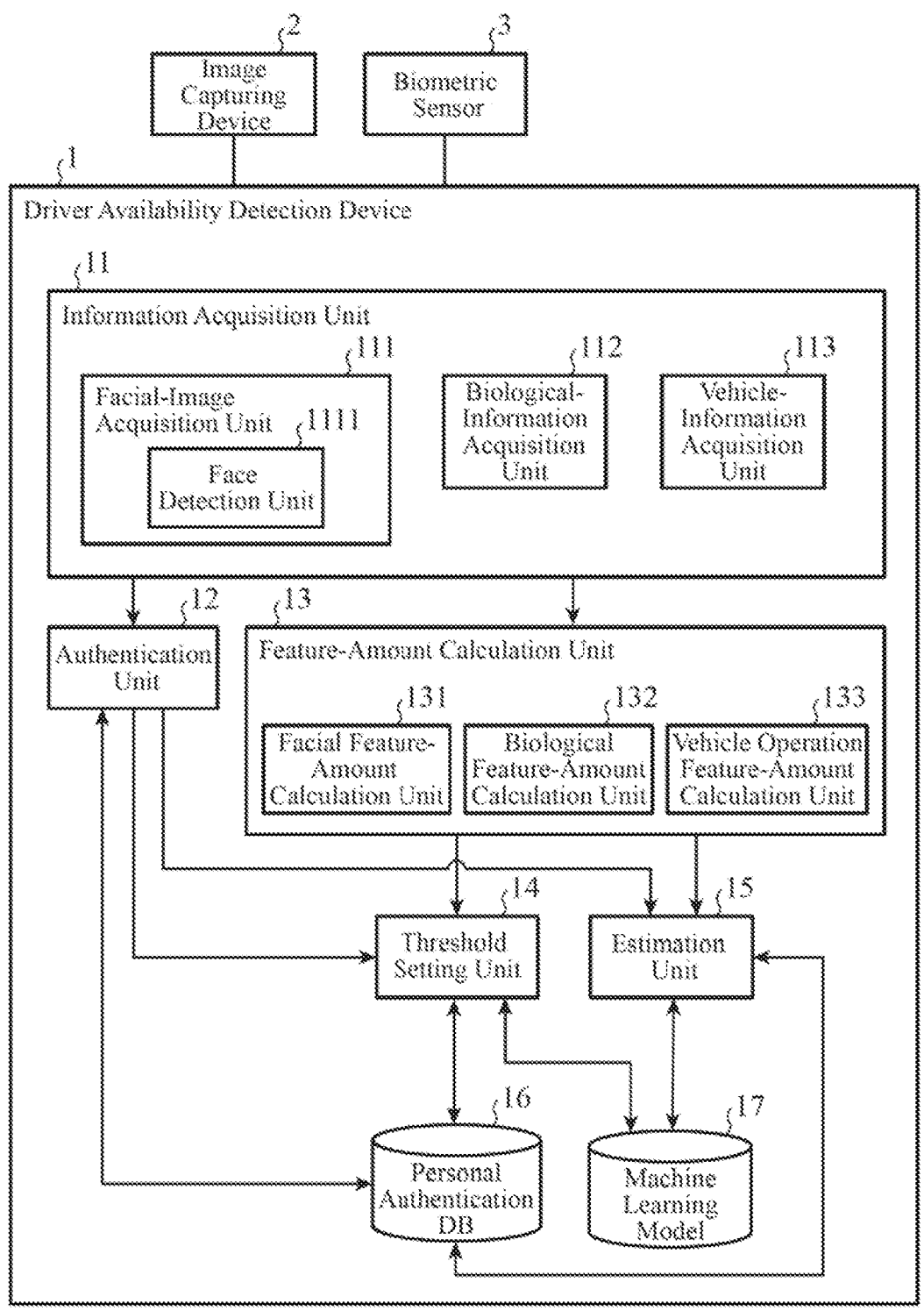
FIG. 1 is a diagram illustrating a configuration example of a driver availability detection device according to a first embodiment.

Hereinafter, embodiments of the present invention will be described in detail with reference to the drawings First Embodiment FIG. 1 is a diagram illustrating a configuration example of a driver availability detection device 1 according to a first embodiment.

The driver availability detection device 1 according to the first embodiment is mounted on a vehicle.

The driver availability detection device 1 estimates an abnormal state of an occupant of a vehicle on the basis of information related to the occupant of the vehicle and a machine-learned model (hereinafter, referred to as "machine learning model") 17. Specifically, the driver availability detection device 1 estimates whether or not the occupant of the vehicle is in an abnormal state on the basis of an abnormal state score obtained by inputting the information related to the occupant of the vehicle to the machine learning model 17. The driver availability detection device 1 estimates that the occupant of the vehicle is in the abnormal state in a case where the abnormal state score is larger than a threshold (hereinafter, referred to as "abnormal-state determination threshold").

When estimating the abnormal state of the occupant of the vehicle, the driver availability detection device 1 sets, before the estimation, the abnormal-state determination threshold on the basis of the abnormal state score obtained by inputting acquired information related to the occupant to the machine learning model 17 within a predetermined time (hereinafter, "first threshold setting time"). After setting the abnormal-state determination threshold, the driver availability detection device 1 performs the estimation process using the set abnormal-state determination threshold.

Details of the setting of the abnormal-state determination threshold or the driver availability detection process in the driver availability detection device 1 will be described later.

In the first embodiment, the occupant of the vehicle is assumed to be, for example, a driver. Hereinafter, the occupant of the vehicle is simply referred to as "occupant". In the first embodiment, the abnormal state of the occupant estimated by the driver availability detection device 1 means a state where the occupant cannot drive appropriately. Specifically, the abnormal slate of the occupant means, for example, a state where the occupant is drowsy, a state where the occupant is drunk, a state where the occupant is tired, or a state where the occupant is careless.

Furthermore, in the first embodiment, the information related to the occupant is, for example, a captured image obtained by capturing the face of the occupant, biological information of the occupant, or vehicle information related to a vehicle operation performed by the occupant on the vehicle. The driver availability detection device 1 estimates the abnormal state of the occupant on the basis of at least one of the captured image, the biological information, or the vehicle information and a machine learning model. Details of the captured image, the biological information, and the vehicle information will be described later.

The driver availability detection device 1 acquires the information related to the occupant from an image capturing device 2, a biometric sensor 3, and a vehicle-information acquisition device (not illustrated). The driver availability detection device 1 is connected to the image capturing device 2, the biometric sensor 3, and the vehicle-information acquisition device via a network.

The image capturing device 2 is installed in a vehicle and captures the face of the occupant. The image capturing device 2 may be, for example, one visible light camera or a plurality of visible light cameras. Furthermore, the image capturing device 2 may be, for example, one infrared camera or a plurality of infrared cameras. Further, the image capturing device 2 may be shared with an image capturing device included in a so-called "driver monitoring system" mounted on a vehicle for monitoring the state of a driver in the vehicle. The image capturing device 2 is only required to be installed to be able to capture at least an area in the vehicle including an area in which the face of the occupant should be present Note that, in a case where the image capturing device 2 is an infrared camera, the image capturing device 2 includes a light source (not illustrated) for irradiating the area including the face of the occupant with image-capturing infrared rays. The light source includes, for example, a light emitting diode (LED).

The biometric sensor 3 is installed, for example, in a vehicle. Specifically, the biometric sensor 3 is, for example, a microwave Doppler sensor, an electrocardiograph embedded in a seat or a steering wheel, or a temperature sensor. In addition, the biometric sensor 3 may be, for example, an occupant-wearable biometric sensor. The occupant-wearable biometric sensor is, for example, a wristwatch-type sphygmograph.

The biometric sensor 3 acquires biological information of the occupant in real time. Specifically, the biological information acquired by the biometric sensor 3 is, for example, information related to the pulse, heartbeat, breathing, iris, or surface temperature of the body.

The vehicle-information acquisition device includes, for example, various sensors that acquire information related to a vehicle. Specifically, the vehicle-information acquisition device is, for example, a vehicle speed sensor, a steering angle sensor, an accelerator position sensor, or a brake position sensor mounted on the vehicle.

The vehicle-information acquisition device acquires, for example, information related to the vehicle speed, steering wheel angle, accelerator position, or brake position as vehicle information.

As illustrated in FIG. 1, the driver availability detection device 1 includes an information acquisition unit 11, an authentication unit 12, a feature-amount calculation unit 13, a threshold setting unit 14, an estimation unit 15, a personal authentication database (hereinafter, referred to as "personal authentication DB") 16, and the machine learning model 17.

The information acquisition unit 11 includes a facial-image acquisition unit 111, a biological-information acquisition unit 112, and a vehicle-information acquisition unit 113. The facial-image acquisition unit 111 includes a face detection unit 111. The feature-amount calculation unit 13 includes a facial feature-amount calculation unit 131, a biological feature-amount calculation unit 132, and a vehicle operation feature-amount calculation unit 133.

The information acquisition unit 11 acquires information related to an occupant of a vehicle. That is, the information acquisition unit 11 acquires information related to a driver.

The facial-image acquisition unit 111 of the information acquisition unit 11 acquires a captured image (hereinafter, referred to as "facial image") obtained by capturing the face of the occupant from the image capturing device 2. At this time, the face detection unit 1111 of the facial-image acquisition unit 111 detects the facial area of the occupant, part of the occupant's face, the face direction of the occupant, the degree of eye opening of the occupant, the line of sight of the occupant, the degree of mouth opening of the occupant, or the like on the basis of the facial image. The face detection unit 1111 can detect the facial area of the occupant, the part of the occupant's face, the face direction of the occupant, the degree of eye opening of the occupant, the line of sight of the occupant, the degree of mouth opening of the occupant, or the like using a known image recognition technology. The part of one's face means, for example, the outer corner of the eye, the inner corner of the eye, the corner of the mouth, or the nose.

The biological-information acquisition unit 112 of the information acquisition unit 11 acquires biological information of the occupant from the biometric sensor 3.

Note that it is assumed that the biological-information acquisition unit 112 acquires the biological information of the occupant from the biometric sensor 3, but this is merely an example. For example, the biological-information acquisition unit 112 may acquire a facial image from the image capturing device 2, and then acquire biological information from the acquired facial image using an existing biometric authentication technology.

The vehicle-information acquisition unit 113 of the information acquisition unit 11 acquires vehicle information from various sensors.

The vehicle-information acquisition unit 113 acquires the vehicle information from various sensors via, for example, a controller area network (CAN).

The information acquisition unit 11 outputs the acquired information related to the occupant to the authentication unit 12 and the feature-amount calculation unit 13. Specifically, the information acquisition unit 11 outputs the facial image acquired by the facial-image acquisition unit 111, the biological information acquired by the biological-information acquisition unit 112, or the vehicle information acquired by the vehicle-information acquisition unit 113 to the authentication unit 12 and the feature-amount calculation unit 13. The information acquisition unit 11 outputs five information related to the facial area of the occupant, the information related to the part of the occupant's face, the information related to the face direction of the occupant, the information related to the degree of eye opening of the occupant, the information related to the line of sight of the occupant, the information related to the degree of mouth opening of the occupant, or the like detected by the face detection unit 1111 in association with the facial image. Note that the information related to the facial area of the occupant is, for example, coordinates on the facial image indicating the facial area of the occupant. In addition, the information related to the part of the occupant's face is, for example, coordinates on the facial image indicating the position of the part of the occupant's face.

The authentication unit 12 authenticates an individual occupant and acquires information (hereinafter, referred to as "personal identification information") for identifying the occupant. In the first embodiment, it is assumed that the personal identification information is, for example, an ID.

Specifically, the authentication unit 12 acquires authentication information, and authenticates the individual occupant by referring to the personal authentication DB 16. The authentication information is, for example, information related to the occupant output from the information acquisition unit 11. In this case, when the information related to the occupant is output from the information acquisition unit 11, the authentication unit 12 authenticates the individual occupant by referring to the personal authentication DB 16. Note that examples of the personal authentication method include image authentication, biometric authentication, and the like.

The personal authentication DB 16 stores information (hereinafter, referred to as "personally identifiable information") that is registered in advance and can identify an individual. Specifically, the personally identifiable information means, for example, information for performing image authentication such as a facial image, or information for performing biometric authentication such as a fingerprint, a palm shape, a vein pattern, or an iris. In addition, the personally identifiable information is only required to be information that can identify the occupant by comparison with information related to the occupant. The personally identifiable information is stored in association with information about who the person is. Here, it is assumed that the information about who the person is an ID.

For example, it is assumed that the authentication unit 12 authenticates the individual occupant by image authentication. In this case, for example, the authentication unit 12 performs face authentication as to whether or not the facial image and the information related to the part of the occupant's thee, the facial image and the information being output from the information acquisition unit 11, is registered in the personally identifiable information.

When the facial image and the information related to the part of the occupant's face, the facial image and the information being output from the information acquisition unit 11, match the facial image and the information related to the facial part registered in the personally identifiable information, respectively, the authentication unit 12 determines that the individual occupant is successfully identified and acquires the corresponding personal identification information, in other words, the ID.

On the other hand, when the facial image and the information related to the part of the occupant's face, the facial image and the information being output from the information acquisition unit 11, do not match the facial image and the information related to the facial part registered in the personally identifiable information, respectively, the authentication unit 12 determines that the individual occupant cannot be identified.

Note that, in the above example, the authentication unit 12 authenticates the individual occupant by image authentication, but for example, the authentication unit 12 may perform biometric authentication as to whether or not the biological information output from the information acquisition unit 11 compares the biological information registered in the personally identifiable information.

In addition, for example, the authentication unit 12 may authenticate the individual occupant by ID card authentication, fingerprint authentication, or the like. In a case where the authentication unit 12 performs the ID card authentication, the authentication unit 12 acquires, for example, information related to an ID card read from a card reader (not illustrated) as authentication information, and compares the information related to the ID card with the personally identifiable information. In a case where the authentication unit 12 performs the fingerprint authentication, the authentication unit 12 acquires fingerprint information from, for example, a fingerprint sensor (not illustrated) as authentication information, and compares the fingerprint information with the personally identifiable information.

In a case where the individual occupant can be identified, the authentication unit 12 outputs the acquired personal identification information to the threshold setting unit 14 and the estimation unit 15.

The feature-amount calculation unit 13 calculates a feature amount related to the occupant on the basis of the information related to the occupant acquired by the information acquisition unit 11. In the first embodiment, the feature amount related to the occupant calculated by the feature-amount calculation unit 13 is an index effective for estimating the abnormal state of the occupant.

The facial feature-amount calculation unit 131 of the feature-amount calculation unit 13 calculates the feature amount related to the occupant on the basis of the facial image of the occupant and the information related to the part of the occupant's face, the facial image and the information being acquired by the facial-image acquisition unit 111 of the information acquisition unit 11. Hereinafter, the feature amount calculated by the facial feature-amount calculation unit 131 is referred to as "facial feature amount".

For example, the facial feature-amount calculation unit 131 calculates, as the facial feature amount, a rate of the information about the degree of eye opening indicating that the eyes of the occupant are open, in other words, the eye opening rate, among the information of the eye opening degree obtained within a predetermined time (hereinafter, referred to as "facial feature-amount determination time") on the basis of the time-series information of the eye opening degree acquired by the facial-image acquisition unit 111. The facial feature-amount calculation unit 131 may calculate a speed of eye opening and closing or a blink interval within the facial feature-amount determination time as the facial feature amount on the basis of the time-series data about the degree of eye opening.

Furthermore, for example, the facial feature-amount calculation unit 131 may calculate the degree of shifting of the line of sight as the facial feature amount on the basis of time-series line-of-sight information acquired by the facial-image acquisition unit 111.

Note that the information acquisition unit 11 stores the acquired information related to the occupant in a storage unit (not illustrated) in time series in association with an acquisition date and time each time the information is acquired. The storage unit may be provided in the driver availability detection device 1 or may be provided in a place that can be referred to by the driver availability detection device 1 outside the driver availability detection device 1. The facial feature-amount calculation unit 131 can acquire the time-series information of the degree of eye opening or the time-series information of the line of sight from the storage unit.

For example, the facial feature-amount calculation unit 131 may calculate a plurality of types of facial feature amounts such as the eye opening rate and shifting of the line of sight. The facial feature-amount calculation unit 131 is only required to calculate a facial feature amount effective for estimating tire abnormal state of the occupant.

The biological feature-amount calculation unit 132 of the feature-amount calculation unit 13 calculates a feature amount related to the occupant on the basis of the biological information acquired by the biological-informal ion acquisition unit 112 of the information acquisition unit 11. Hereinafter, the feature amount calculated by the biological feature-amount calculation unit 132 is referred to as "biological feature amount".

For example, the biological feature-amount calculation unit 132 calculates, as the biological feature amount, an average respiratory interval within a predetermined time (hereinafter, referred to as "biological feature-amount determination time") on the basis of the respiratory rate of the occupant acquired by the biological-information acquisition unit 112.

Furthermore, for example, the biological feature-amount calculation unit 132 may calculate an average value or a standard deviation of the heart rate within the biological feature amount determination time as the biological feature amount on the basis of the heart rate.

Note that the biological feature-amount calculation unit 132 can acquire the past respiratory rate of the occupant or the past bean rate of the occupant from the storage unit.

For example, the biological feature-amount calculation unit 132 may calculate a plurality of types of biological feature amounts such as an average respiratory interval and a heart rate within the biological feature-amount determination time. The biological feature-amount calculation unit 132 in only required to calculate a biological feature amount effective for estimating the abnormal state of the occupant.

The vehicle operation feature-amount calculation unit 133 of the feature-amount calculation unit 13 calculates a feature amount related to the occupant on the basis of the vehicle information acquired by the vehicle-information acquisition unit 113. Hereinafter, the feature amount calculated by the vehicle operation feature-amount calculation unit 133 is referred to as "vehicle operation feature amount".

For example, the vehicle operation feature-amount calculation unit 133 calculates, as the vehicle operation feature amount, a change amount of a brake position within a predetermined time (hereinafter, referred to as "vehicle operation feature-amount determination time") on the basis of the information related to the brake position acquired by the vehicle-information acquisition unit 113.

Furthermore, for example, the vehicle operation feature-amount calculation unit 133 may calculate, as the vehicle operation feature amount, a change amount of as steering wheel angle within the vehicle operation feature-amount determination time on the basis of the information related to the steering wheel angle acquired by the vehicle-information acquisition unit 113.

Note that the vehicle operation feature-amount calculation unit 133 can acquire information related to the past brake position or information related to the past steering wheel angle from the storage unit.

The vehicle operation feature-amount calculation unit 133 may calculate a plurality of types of vehicle operation feature amounts such as the change amount of the brake position and the change amount of the steering wheel angle, for example. The vehicle operation feature-amount calculation unit 133 is only required to calculate a vehicle operation feature amount effective for estimating the abnormal state of the occupant.

The feature-amount calculation unit 13 outputs the calculated feature amount related to the occupant to the threshold setting unit 14 and the estimation unit 15.

The threshold setting unit 14 sets an abnormal-state determination threshold for estimating the abnormal state of the occupant on the basis of an abnormal state score obtained by inputting the feature amount calculated by the feature-amount calculation unit 13 to the machine learning model 17 within a predetermined time (hereinafter referred to as "first threshold setting time").

The first threshold setting time is a time that is set in order to perform a process of setting the abnormal-state determination threshold in the driver availability detection device 1 and in which it is assumed that the occupant is in a normal state. The process of setting the abnormal-state determination threshold is a process that is performed before estimating the abnormal state of the occupant in the driver availability detection device 1.

The first threshold setting time is set in advance. It is assumed in the first embodiment that the first threshold setting time is a time from a start point where driving of the vehicle starts to an end point where a predetermined constant time has elapsed. For example, the first threshold setting time is ten minutes from the start of driving of the vehicle. In the first embodiment, the start of driving of the vehicle means a time when a certain occupant whose abnormal state is to be estimated starts to drive the vehicle, and does not simply mean a time when an engine of the vehicle is driven or the like. For example, it is assumed that, after a certain occupant drives the vehicle and a certain period of time elapses, because the certain occupant switches driving to another occupant while the engine remains driven, so that the occupant whose abnormal state is to be estimated is changed. In this case, the time point at which the other occupant starts to drive the vehicle after switching driving is regarded as the start of driving of the vehicle. The first threshold setting time is set by using the start of driving of the vehicle when the other occupant starts to drive the vehicle as a start point.

Note that the threshold setting unit 14 can detect the start of driving of the vehicle by various known methods. For example, the threshold setting unit 14 may detect the start of driving of the vehicle by the start of the engine of the vehicle, or may detect the start of driving of the vehicle on the basis of the facial image acquired from the image capturing device 2.

Here, the machine learning model 17 will be described.

The machine learning model 17 is a machine learning model that outputs an abnormal state score used for estimating the abnormal state of the occupant when information related to the occupant is input.

The machine learning model 17 is generated in advance by, for example, a learning device (not illustrated) that performs learning in machine learning.

The learning device performs a learning process of performing learning using teacher data and a correct answer label of an abnormal state. The correct answer label of the abnormal state is a label indicating the abnormal state or a label indicating the normal state.

The learning device acquires information related to a plurality of occupants, the information being collected in advance. Specifically, for example, an administrator or the like collects in advance information related to a plurality of test subjects when the test subjects get on a vehicle and a test run is performed. The learning device acquires information related to the plurality of test subjects collected by the administrator or the like as the information related to the plurality of occupants. Note that the information related to the occupant acquired by the learning device is the same type of information as the information related to the occupant acquired by the information acquisition unit 11 described above. That is, the information related to the occupant acquired by the learning device is one or more of the facial image of the occupant, the biological information, or the vehicle information.

The learning device acquires the information related to the occupants, and individually calculates feature amounts related to the occupants on the basis of the acquired information related to the occupants. The feature amount related to the occupant calculated by the learning device is the same type of feature amount as the feature amount related to the occupant calculated by the feature-amount calculation unit 13 described above. That is, the feature amount calculated bye the learning device is any one or more of the facial feature amount, the biological feature amount, or the vehicle operation feature amount. The learning device uses the calculated feature amount as teacher data.

Figure 2:
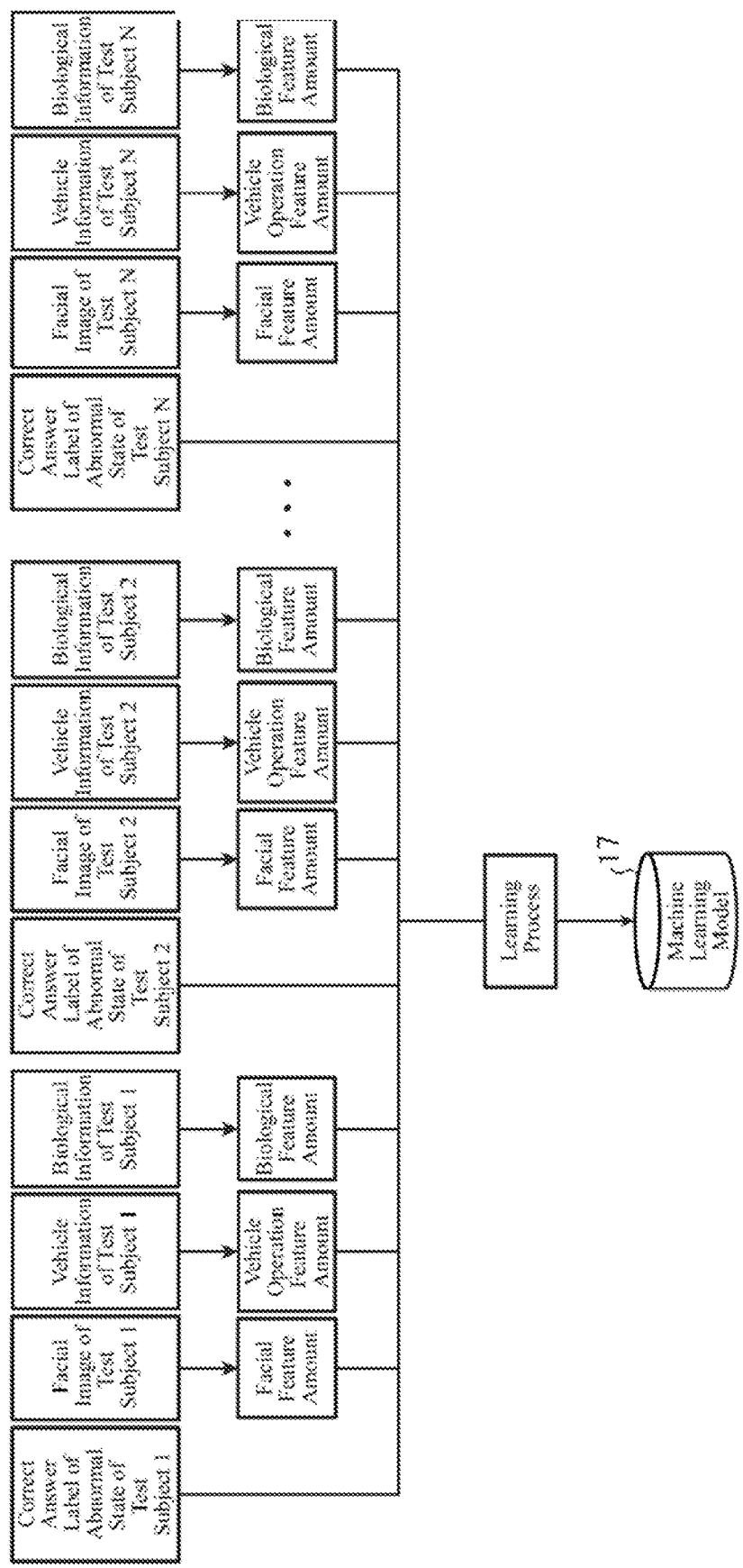
FIG. 2 is a diagram for explaining the concept of a process in which a learning device performs a learning process to generate a machine learning model in the first embodiment.

FIG. 2 is a diagram for explaining the concept of a process in which a learning device performs a learning process to generate the machine learning model 17 in the first embodiment.

As illustrated in FIG. 2, the learning device performs a learning process on information related to a plurality of occupants collected in advance with a correct answer label of an abnormal state, and generates the machine learning model 17. In FIG. 2, it is assumed that the learning device generates the machine learning model 17 on the basis of information related to N occupants. The N occupants include an occupant in a normal state and an occupant in an abnormal state.

The larger the number "N" of occupants, the more preferable it is. As the machine learning model 17 is generated on the basis of information related to more occupants, the accuracy of estimation when the abnormal state is estimated on the basis of the machine learning model 17 in the driver availability detection device 1 is improved.

Further, the attributes of the N occupants are desirably various attributes. In the first embodiment, the attribute of the occupant is, for example, gender or age.

The technique of the learning method in the learning process performed by the learning device is not limited. For example, the learning device may perform the learning process by deep learning or may perform the learning process by decision tree learning.

Furthermore, here, the learning device generates the machine learning model 17 by supervised learning in which learning is performed with the correct answer label, but this is merely an example. The learning device may generate the machine learning model 17 by unsupervised learning.

In addition, here, the machine learning model 17 is included in the driver availability detection device 1, but this is merely an example. The machine learning model 17 may be provided in a place that can be referred to by the driver availability detection device 1 outside the driver availability detection device 1.

The description returns to FIG. 1.

As described above, the threshold setting unit 14 sets the abnormal-state determination threshold for estimating the abnormal state of die occupant on the basis of the abnormal state score obtained by inputting the feature amount calculated by the feature-amount calculation unit 13 to the machine learning model 17 within the first threshold setting time.

In the first embodiment, the threshold setting unit 14 sets the maximum value among one or more abnormal state scores obtained within the first threshold setting time as the abnormal-state determination threshold. In this time, the threshold setting unit 14 may set the abnormal-state determination threshold by providing a buffer to the maximum value among one or more abnormal state scores obtained within the first threshold setting time. Specifically, the threshold setting unit 14 may set the maximum value of the abnormal state score+α as the abnormal-state determination threshold. α is assumed to be larger than 0. In addition, for example, the threshold setting unit 14 may set, as the abnormal-state determination threshold, a value obtained by multiplying the maximum value among one or more abnormal state scores obtained within the first threshold setting time by a coefficient.

Since the first threshold setting time is a time in which the occupant is assumed to be in a normal state, the abnormal state score obtained within the first threshold setting time is regarded as an abnormal state score obtained in a case where the occupant is in the normal state. In other words, the occupant can be regarded as being in the normal state if the abnormal state score is within the maximum value of the abnormal state score obtained within the first threshold setting time. The threshold setting unit 14 can set the abnormal-state determination threshold that can appropriately estimate the abnormal state of the occupant by setting the maximum value among the abnormal state scores obtained in a case where the occupant is in the normal state as the abnormal-state determination threshold.

Note that, however, the maximum value of the abnormal state score obtained within the first threshold setting time is not necessarily the maximum value of the abnormal state score that can be obtained in a case where the occupant is in the normal state. For example, in a case where the abnormal state score obtained within the first threshold setting time is somewhat exceeded, the occupant may be in the normal state. The threshold setting unit 14 can reduce the possibility of determining that the occupant is in the abnormal state even though the occupant is in the normal state by setting the abnormal-state determination threshold with a margin in the abnormal state score, for example, by setting the maximum value of the abnormal state score+α as the abnormal-state determination threshold.

The threshold setting unit 14 stores the set abnormal-state determination threshold in the storage unit in association with the personal identification information output from the authentication unit 12.

As described above, in the first embodiment, the threshold setting unit 14 assumes that the occupant is not in the abnormal state, in other words, the occupant is in the normal state for the first threshold setting time. The threshold setting unit 14 inputs the feature amount related to the occupant to the machine learning model 17 during the time and acquires one or more abnormal state scores. The threshold setting unit 14 then sets the abnormal-state determination threshold for the occupant on the basis of the maximum value of one or more abnormal state scores acquired.

Note that, as described above, the abnormal state score is output from the machine learning model 17 for the first threshold setting time during which the threshold setting unit 14 performs the process of setting the abnormal-state determination threshold. However, the driver availability detection device 1 does not estimate the abnormal state of the occupant on the basis of the abnormal state score for the first threshold setting time during which the threshold setting unit 14 performs the process of setting the abnormal-state determination threshold. For example, the driver availability detection device 1 determines whether to estimate the abnormal state of the occupant on the basis of whether the estimatable flag is "1" or "0". In a case where the estimatable flag is "1", the driver availability detection device 1 determines to estimate the abnormal state of the occupant. On the other hand, in a case where the estimatable flag is "0", the driver availability detection device 1 determines not to estimate the abnormal state of the occupant. The determination is performed, for example, by a control unit of the driver availability detection device 1. Note that in the driver availability detection device 1, the estimation of the abnormal state of the occupant is performed by the estimation unit 15 to be described later.

When completing the setting of the abnormal-state determination threshold, the threshold setting unit 14 sets the estimatable flag "1". Specifically, in a case where the estimatable flag is "0", the control unit causes the threshold setting unit 14 to perform the process of setting the abnormal-state determination threshold. As described above, the threshold setting unit 14 sets the abnormal-state determination threshold by performing the process of setting the abnormal-state determination threshold, stores the abnormal-state determination threshold in the personal authentication DB 16 in association with the ID, and sets the estimatable flag to "1".

Since the threshold setting unit 14 sets the estimatable flag to "1" when completing the setting of the abnormal-state determination threshold, the estimatable flag is "0" while the threshold sitting unit 14 does not set the abnormal-state determination threshold in the driver availability detection device 1.

In a case where the estimatable flag is "0", the control unit of the driver availability detection device 1 does not cause the estimation unit 15 to estimate the abnormal state of the occupant. As a result, in the driver availability detection device 1, even if the abnormal state score is output from the machine learning model 17 for the first threshold setting time, the driver availability detection device 1 can be prevented from estimating the abnormal state of the occupant.

When the threshold setting unit 14 sets the estimatable flag to "1" and then the control unit determines that the estimatable flag is "1", the control unit causes the estimation unit 15 to estimate the abnormal state of the occupant. That is, in the driver availability detection device 1, after the threshold setting unit 14 sets the abnormal-state determination threshold, the abnormal state of the occupant is estimated.

As described above, the threshold setting unit 14 performs the process of setting the abnormal-state determination threshold in a case where the estimatable flag is "0" on the basis of the control of the control unit. In this manner, the threshold setting unit 14 is only required to perform the process of setting the abnormal-state determination threshold once at the start of driving of the vehicle.

Note that the estimatable flag is initialized at, for example, a timing when driving of the vehicle is stopped or a timing when the occupant whose abnormal state is to be estimated changes, and becomes "0". For example, the control unit initializes the estimatable flag.

The estimation unit 15 estimates that the occupant is in the abnormal state in a case where the abnormal state score obtained by inputting the feature amount related to the occupant calculated by the feature-amount calculation unit 13 to the machine learning model 17 is larger than the abnormal-state determination threshold set by the threshold setting unit 14.

Specifically, the estimation unit 15 inputs the feature amount related to the occupant calculated by the feature-amount calculation unit 13 to the machine learning model 17, and acquires the output abnormal state score. The estimation unit 15 compares the acquired abnormal state score with the abnormal-state determination threshold stored in the storage arm by the threshold setting unit 14. At this time, the estimation unit 15 compares the personal identification information output from the authentication unit 12 with the personal identification information associated with the abnormal-state determination threshold in the storage unit, and acquires the abnormal-state determination threshold associated with the matched personal identification information from the storage unit as the abnormal-state determination threshold for estimating the abnormal state of the occupant.

In a case where the abnormal state score is larger than the abnormal-state determination threshold, the estimation unit 15 estimates that the occupant is in the abnormal state. On the other hand, in a case where the abnormal state score is less than or equal to the abnormal-state determination threshold, the estimation unit 15 estimates that the occupant is in the normal state.

The personal authentication DB 16 stores the personally identifiable information.

The personal authentication DB 16 is provided in, for example, the storage unit.

An operation of the driver availability detection device 1 according to the first embodiment will be described.

Figure 3:
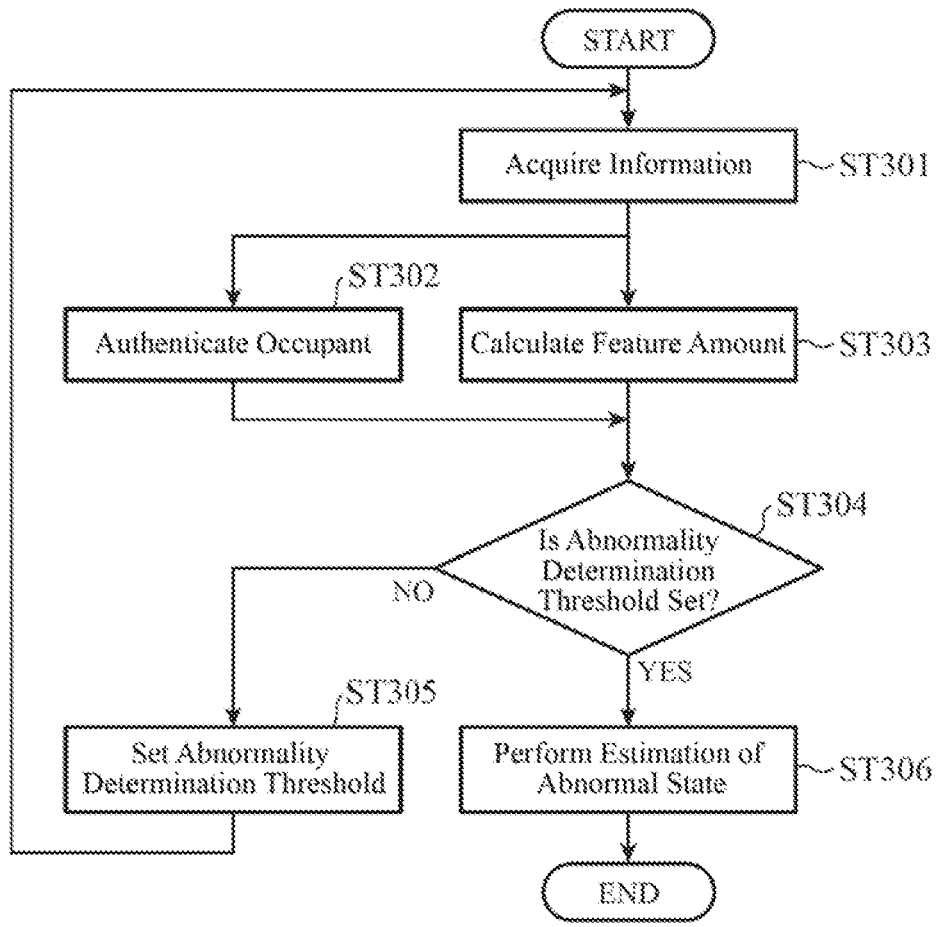
FIG. 3 is a flowchart for explaining an operation of the driver availability detection device according to the first embodiment.

FIG. 3 is a flowchart for explaining the operation of the driver availability detection device 1 according to the first embodiment.

The information acquisition unit 11 acquires information related to an occupant (step ST301).

Figure 4:
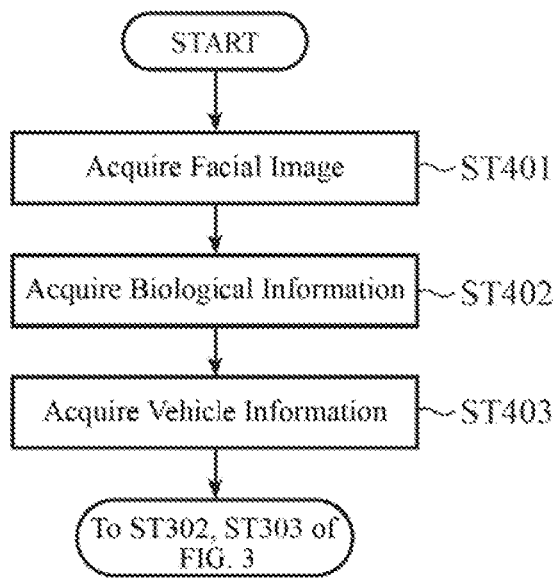
FIG. 4 is a flowchart for explaining a specific operation of step ST301 in FIG. 3.

Here, FIG. 4 is a flowchart for explaining a specific operation of step ST301 in FIG. 3.

The facial-image acquisition unit 111 of the information acquisition unit 11 acquires a facial image from the image capturing device 2 (step ST401).

The biological-information acquisition unit 112 of the information acquisition unit 11 acquires biological information of the occupant from the biometric sensor 3 (step ST402).

The vehicle-information acquisition unit 113 of the information acquisition unit 11 acquires vehicle information from various sensors (step ST403).

The information acquisition unit 11 outputs the acquired information related to the occupant to the authentication unit 12 and the feature-amount calculation unit 13.

The description returns to the flowchart of FIG. 3.

The authentication unit 12 authenticates the individual occupant and acquires personal identification information (step ST302). In a case where the individual occupant can be identified, the authentication unit 12 outputs the acquired personal identification information to the threshold setting unit 14 and the estimation unit 15.

The feature-amount calculation unit 13 calculates the feature amount related to the occupant on the basis of the information related to the occupant acquired by the information acquisition unit 11 (step ST303).

Figure 5:
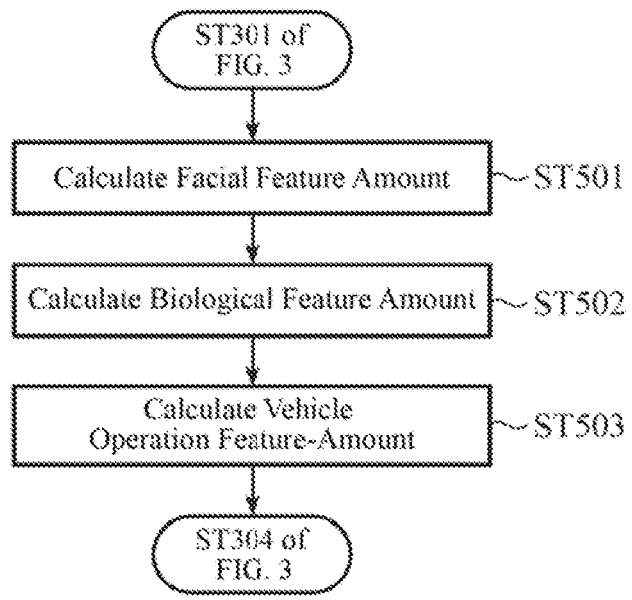
FIG. 5 is a flowchart for explaining a specific operation of step ST303 in FIG. 3.

Here, FIG. 5 is a flowchart for explaining a specific operation of step ST303 in FIG. 3.

The facial feature-amount calculation unit 131 of the feature-amount calculation unit 13 calculates the facial feature amount of the occupant on the basis of a facial image of the occupant and information related to the part of the occupant's face, the facial image and the information being acquired by the facial-image acquisition unit 111 of the information acquisition unit 11 in step ST401 of FIG. 4 (step ST501).

The biological feature-amount calculation unit 132 of the feature-amount calculation unit 13 calculates a biological feature amount on the basis of the biological information acquired by the biological-information acquisition unit 112 of the information acquisition unit 11 in step ST402 of FIG. 4 (step ST502).

The vehicle operation feature-amount calculation unit 133 of the feature-amount calculation unit 13 calculates a vehicle operation feature amount on the basis of the vehicle information acquired by the vehicle-information acquisition unit 113 in step ST403 of FIG. 4 (step ST503).

The feature-amount calculation unit 13 outputs the calculated feature amount related to the occupant to the threshold setting unit 14 and the estimation unit 15.

The description returns to the flowchart of FIG. 3.

Figure 6:
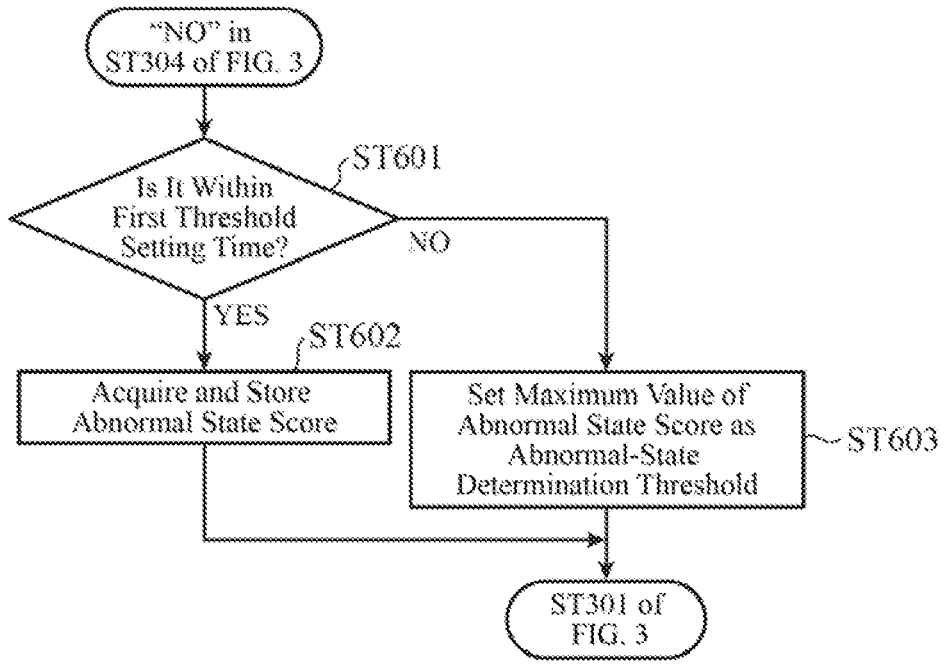
FIG. 6 is a flowchart for explaining a specific operation of step ST305 in FIG. 5.

The control unit determines whether or not the abnormal-state determination threshold is set (step ST304). Specifically, the control unit determines whether or not the estimatable flag is "1". Note that since the abnormal-state determination threshold is not set before the operation to be described later with reference to FIG. 6 is performed, the control unit determines that the abnormal-state determination threshold is not set. Since the abnormal-state determination threshold has been set after the operation to be described later with reference to FIG. 6 is performed, the control unit determines that the abnormal-state determination threshold is set.

If the control unit determines in step ST304 that the abnormal-state determination threshold is not set, in other words, if the control unit determines that the estimatable flag is "0" ("NO" in step ST304), the operation of the flowchart of FIG. 3 proceeds to step ST305.

The threshold setting unit 14 then sets the abnormal-state determination threshold for estimating the abnormal state of the occupant on the basis of the abnormal state score obtained by inputting the feature amount related to the occupant calculated in step ST303 by the feature-amount calculation unit 13 to live machine learning model 17 within the first threshold setting time (step ST305).

Here, FIG. 6 is a flowchart for explaining a specific operation of step ST305 in FIG. 3.

First, the threshold setting unit 14 determines whether or not it is within the first threshold setting time (step ST601).

If the threshold setting unit 14 determines in step ST601 that it is within the first threshold setting time ("YES" in step ST601), the threshold setting unit 14 acquires the abnormal state score output by inputting the feature amount related to the occupant most recently calculated in step ST303 of FIG. 3 by the feature-amount calculation unit 13 to the machine learning model 17. The threshold setting unit 14 then stores the acquired abnormal state score in the storage unit (step ST602). Thereafter, the operation of the flowchart of FIG. 6 returns to step ST301 of FIG. 3, and when the operation of step ST301 is performed, the process proceeds to the operation of steps subsequent to step ST301 again. The threshold setting unit 14 performs the operation of step ST602 thereafter until the first threshold setting time elapses ("NO" in step ST601). As a result, one or more abnormal state scores obtained within the first threshold setting time by the threshold setting unit 14 are stored in the storage unit.

When the first threshold setting time elapses ("NO" in step ST601), the threshold setting unit 14 sets the abnormal-state determination threshold on the basis of the abnormal state scores stored in file storage unit. Specifically, the threshold setting unit 14 sets the maximum value among the abnormal state scores stored in the storage unit, in other words, one or more abnormal state scores obtained within the first threshold setting time as the abnormal-state determination threshold (step ST603).

The threshold setting unit 14 stores the set abnormal-state determination threshold in the storage unit in association with the personal identification information output from the authentication unit 12.

The description returns to the flowchart of FIG. 3.

If the control unit determines in step ST304 that the abnormal-state determination threshold is set, in other words, if the control unit determines that the estimatable flag is "1" ("YES" in step ST304), the operation of the flowchart of FIG. 3 proceeds to step ST306.

The estimation unit 15 then estimates the abnormal state of the occupant on the basis of the abnormal state score obtained inputting the feature amount related to the occupant calculated in step ST303 by the feature-amount calculation unit 13 to the machine learning model 17 (step ST306).

Figure 7:
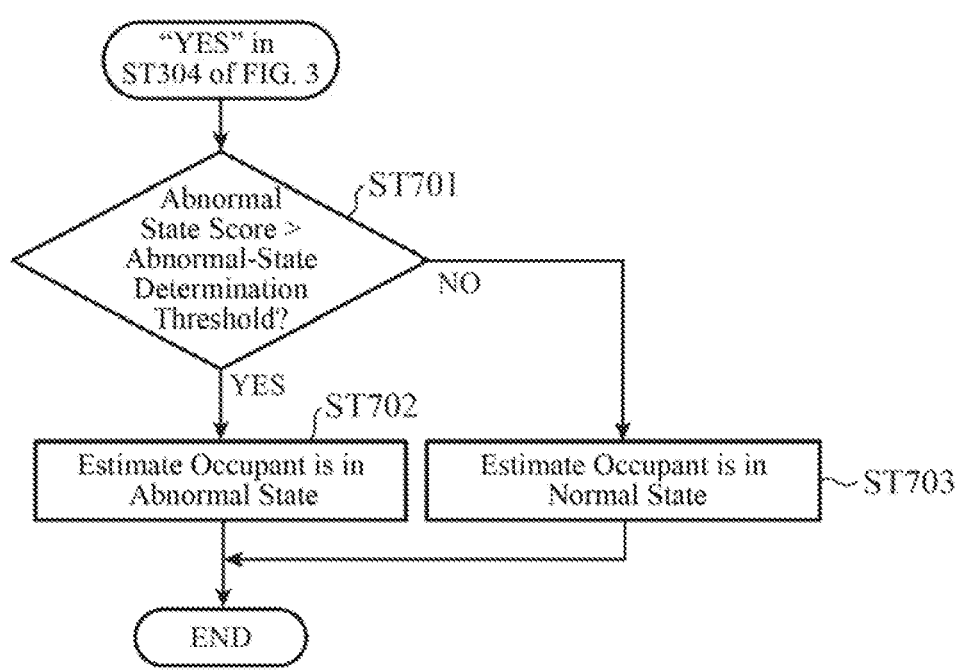
FIG. 7 is a flowchart for explaining a specific operation of step ST306 in FIG. 3.

Here, FIG. 7 is a flowchart for explaining a specific operation of step ST306 in FIG. 3.

The estimation unit 15 acquires the abnormal state score output by inputting the feature amount related to the occupant most recently calculated in step ST303 of FIG. 3 by the feature-amount calculation unit 13 to the machine learning model 17. The estimation unit 15 then determines whether or not the acquired abnormal state score is larger than the abnormal-state determination threshold set in step ST305 of FIG. 3 by the threshold setting unit 14 (step ST701).

If it is determined in step ST701 that the abnormal state score is larger than the abnormal-state determination threshold ("YES" in step ST701), the estimation unit 15 determines that the occupant is in the abnormal state (step ST702).

On the other hand, if it is determined in step ST701 that the abnormal state score is less than or equal to the abnormal state determination threshold ("NO" in step ST701), the estimation unit 15 estimates that the occupant is not in the abnormal state, in other words, the occupant is in the normal state (step ST703).

As described above, the driver availability detection device 1 according to the first embodiment assumes that the occupant is in the normal state for the first threshold setting time, and sets the abnormal-slate determination threshold on the basis of the maximum value of the abnormal state score obtained by inputting the feature amount related to the occupant to the machine learning model 17.

After setting the abnormal-state determination threshold, the driver availability detection device 1 acquires the abnormal state score by inputting the feature amount related to the occupant to the machine learning model 17. In a case where the acquired abnormal state score is larger than the abnormal-state determination threshold, the driver availability detection device 1 estimates that the occupant is in the abnormal state. The driver availability detection device 1 does not estimate whether or not the occupant is in the abnormal state using a fixed threshold, but sets the abnormal-state determination threshold for each occupant, and estimates whether or not the occupant is in the abnormal state using the abnormal-state determination threshold. Consequently, when estimating whether or not the occupant is in the abnormal state, the driver availability detection device 1 can prevent erroneous estimation of the abnormal state of the occupant.

Note that in the operation described in the flowchart of FIG. 3, in a case where the authentication unit 12 cannot identify the individual occupant in step ST302 of FIG. 3, the operation of the driver availability detection device 1 proceeds to the operation of step ST304 and subsequent steps of FIG. 3, similarly to the case where the authentication unit 12 can identify the individual occupant. Note that, however, in a case where the authentication unit 12 cannot identify the individual occupant, the threshold setting unit 14 cannot associate the set abnormal-state determination threshold with the personal identification information when storing the set abnormal-state determination threshold in the storage unit. When acquiring the abnormal-state determination threshold from the storage unit, the estimation unit 15 acquires, for example, the latest abnormal-state determination threshold stored in the storage unit.

As described above, the driver availability detection device 1 performs the operation described in the flowchart of FIG. 3 from the start of driving of the vehicle to the end of driving of the vehicle, for example, at a timing when the facial-image acquisition unit 111 acquires one frame of a facial image from the image capturing device 2. The end of driving of the vehicle includes, for example, stopping of driving of the vehicle and a change of an occupant whose abnormal state is to be estimated.

In this case, the estimation unit 15 frequently estimates the abnormal state of the occupant. However, as described above, the abnormal state of the occupation is, for example, a state where the occupant is drowsy, a state where the occupant is drunk, a state where the occupant is tired, or a state where the occupant is careless, and the abnormal state does not change frequently.

Consequently, for example, the estimation unit 15 may estimate that the occupant is in the abnormal state when the rate at which the occupant is estimated to be in the abnormal state is larger than or equal to a threshold during a predetermined time (hereinafter referred to as "driver availability detection time"), and thereafter, does not have to estimate the abnormal state of the occupant until the driving of the vehicle is ended. The driver availability detection time is five minutes, ten minutes, or the like.

According to the first embodiment described above, in the driver availability detection device 1, the information input to the machine learning model 17 is the feature amount related to the occupant calculated by the feature-amount calculation unit 13, but this is merely an example. For example, in the driver availability detection device 1, the information input to the machine learning model 17 may be information related to the occupant acquired by the information acquisition unit 11. In this case, the driver availability detection device 1 can be configured not to include the feature-amount calculation unit 13.

Note, however, that when the driver availability detection device includes the feature-amount calculation unit 13 and inputs the feature amount related to the occupant, the feature amount having a large correlation with the estimation of the abnormal state, to the machine learning model 17, the accuracy of estimation at the time of estimating the abnormal state of the occupant can be improved as compared with the case where the information related to the occupant is directly input to the machine learning model 17.

Note that, in a case where the information input to the machine learning model 17 is the information related to the occupant in the driver availability detection device 1, the learning device sets the information related to the occupant as teacher data.

As described above, according to the first embodiment, the driver availability detection device 1 that estimates the abnormal state of the occupant of the vehicle on the basis of the information related to the occupant and the machine learning model 17 includes the information acquisition unit 11 that acquires the information related to the occupant and the threshold setting unit 14 that sets the abnormal-state determination threshold for estimating the abnormal state of the occupant on the basis of the abnormal state score obtained by inputting the information related to the occupant acquired by the information acquisition unit 11 to the machine learning model 17 within the first threshold setting time.

Consequently, when estimating whether or not the occupant is in the abnormal state, the driver availability detection device 1 can prevent erroneous estimation of the abnormal state of the occupant.

Second Embodiment

In the first embodiment, one machine learning model 17 is generated in advance on the basis of information related to a plurality of occupants.

However, the facial feature amount, the biological feature amount, or the like of the occupant in a case where the occupant is in a normal state or an abnormal state is different for each occupant. For example, there are some occupants who are not in the abnormal state even if they are drowsy, whereas there are some occupants who are not in the abnormal state even if the pulse rate is significantly reduced. In addition, there are some occupants who are not in the abnormal state even if a change in steering wheel angle is large. As described above, for example, even in the same abnormal state, the facial feature amounts or the biological feature amounts of the plurality of occupants have various variations. As a result, when the feature amounts related to the plurality of occupants based on the information related to the plurality of occupants are input to the machine learning model 17 and learning is performed in a learning device, there is a possibility that a process of rounding the input feature amounts or the like is performed. The machine learning model 17 generated by performing the process of rounding the feature amount or the like can be a machine learning model in which the abnormal state cannot be appropriately estimated when the abnormal state of the occupant is estimated on the basis of the machine learning model 17. The driver availability detection device 1 may not be able to appropriately set an abnormal-state determination threshold for appropriately estimating the abnormal state from the machine learning model in which the abnormal state cannot be appropriately estimated.

Consequently, in a second embodiment, it is assumed that a plurality of machine learning models 17 are generated in advance on the basis of information related to a plurality of occupants. Specifically, it is assumed that N machine learning models (1 to N) 17 are generated in advance on the basis of information related to N occupants. A driver availability detection device 1*a* sets the abnormal-state determination threshold on the basis of the N machine learning models (1 to N) 17, and estimates the abnormal state of the occupant using the set abnormal-state determination threshold.

The driver availability detection device 1*a* according to the second embodiment is assumed to be mounted on a vehicle similarly to the driver availability detection device 1 according to the first embodiment.

Figure 8:
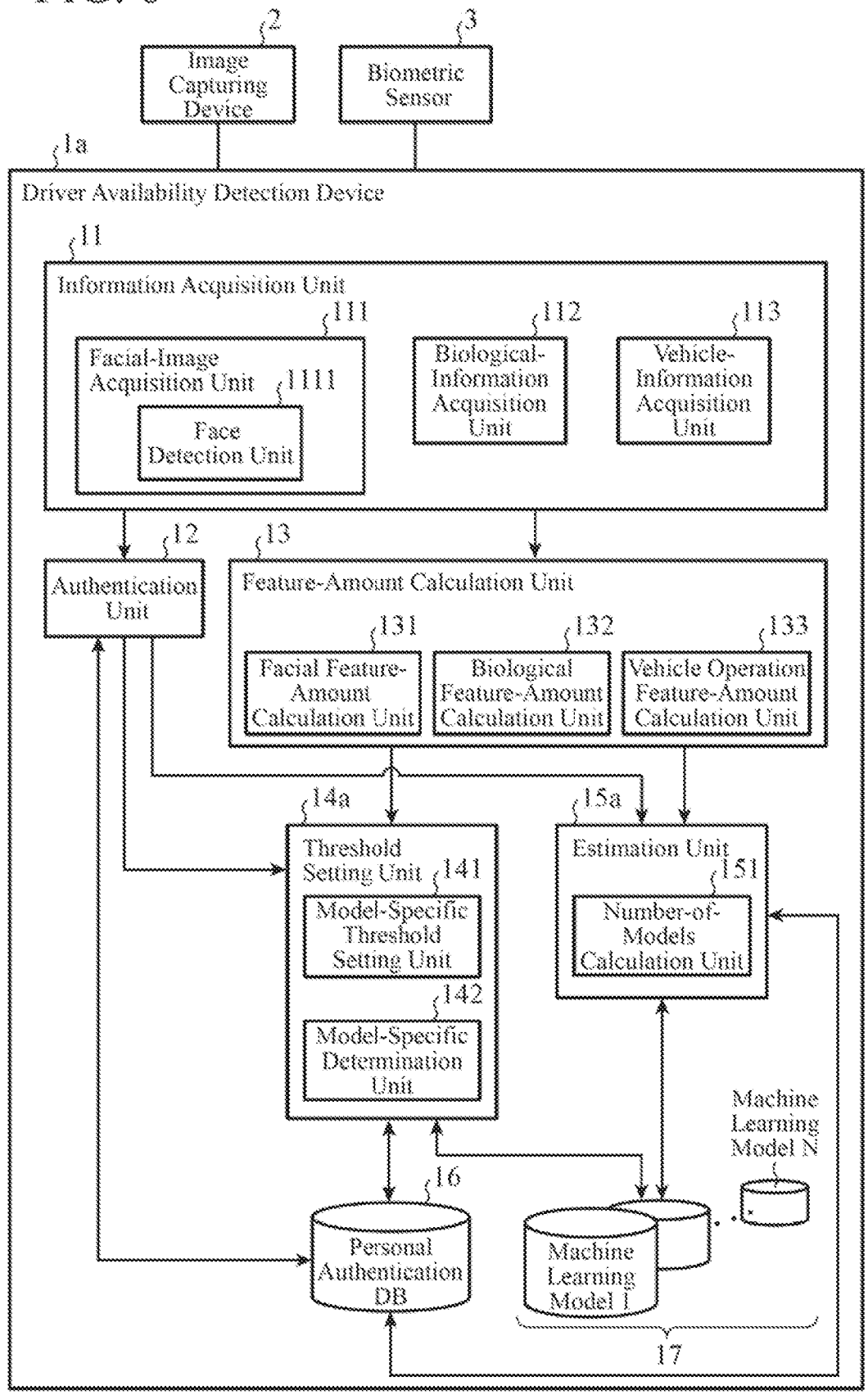
FIG. 8 is a diagram illustrating a configuration example of a driver availability detection device according to a second embodiment.

FIG. 8 is a diagram illustrating a configuration example of the driver availability detection device 1*a* according to the second embodiment.

In the configuration example of the driver availability detection device 1*a* according to the second embodiment, the same components as those of the driver availability detection device 1 described in the first embodiment with reference to FIG. 1 are denoted by the same reference numerals, and redundant description will be omitted.

The driver availability detection device 1*a* according to the second embodiment is different from the driver availability detection device 1 according to the first embodiment in that a threshold setting unit 14*a* includes a model-specific threshold setting unit 141 and a model-specific determination unit 142.

In addition, the driver availability detection device 1*a* according to the second embodiment is different from the driver availability detection device 1 according to the first embodiment in that an estimation unit 15*a* includes a number-of-models calculation unit 151.

Furthermore, the driver availability detection device to according to the second embodiment is different from the driver availability detection device 1 according to the first embodiment in that it includes a plurality of machine learning models (1 to N) 17. Note that, here, it is assumed that the machine learning models (1 to N) 17 are provided in the driver availability detection device 1*a*, but this is merely an example. The machine learning models (1 to N) 17 may be provided in a place that can be referred to by the driver availability detection device 1*a* outside the driver availability detection device 1*a*.

Here, the machine learning models (1 to N) 17 will be described.

The machine learning models (1 to N) 17 are generated in advance by a learning device as in the first embodiment.

Figure 9:
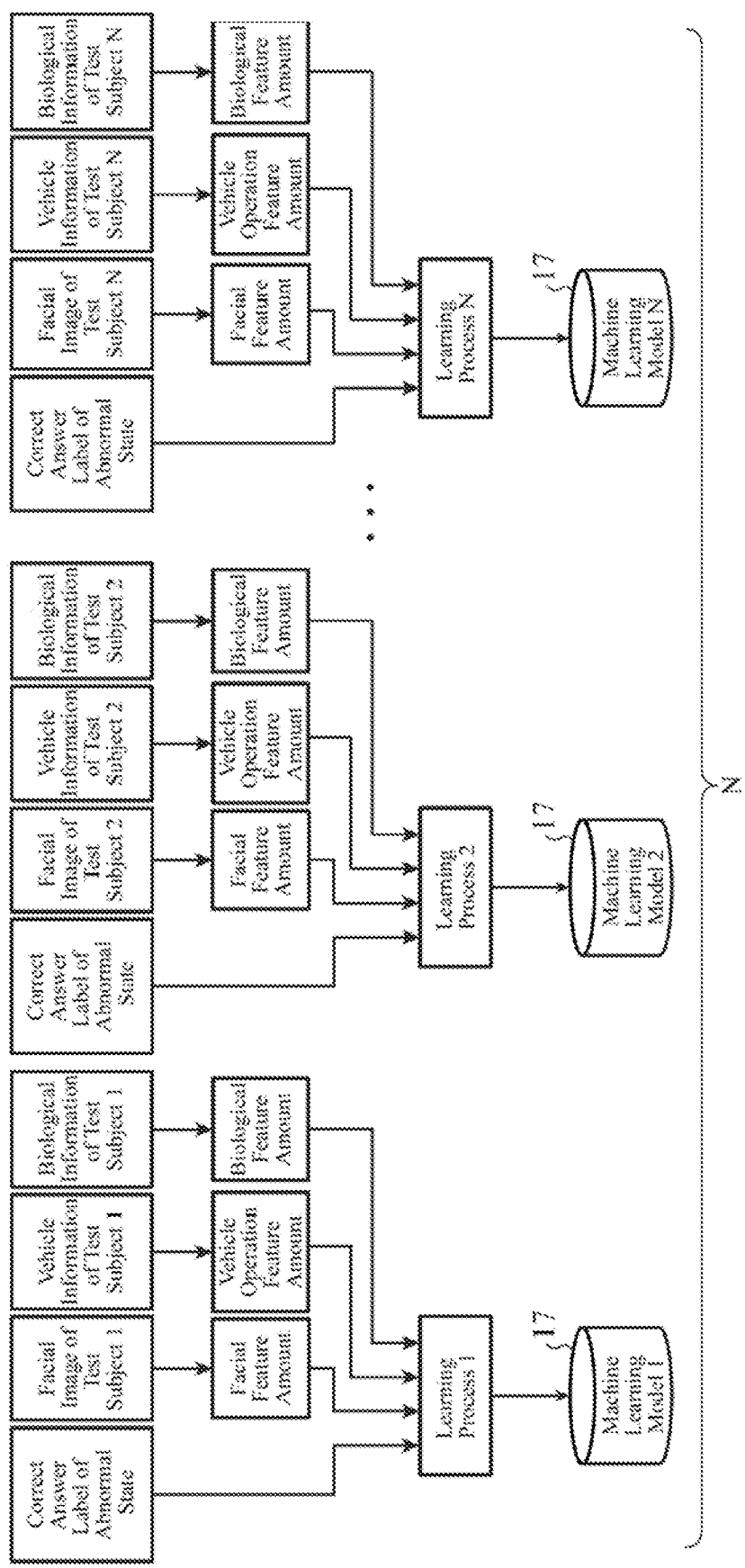
FIG. 9 is a diagram for explaining the concept of a process in which a learning device performs a learning process to generate a machine learning model in the second embodiment.

FIG. 9 is a diagram for explaining the concept of a process in which the learning device performs a learning process to generate the machine learning models (1 to N) 17 in the second embodiment.

In the first embodiment, the learning device collectively performs the learning process on information related to a plurality of occupants collected in advance with correct answer labels of an abnormal state, and generates one machine learning model 17 (see FIG. 2).

On the other hand, in the second embodiment, the learning device performs the learning process on each piece of the information related, to a plurality of occupants collected in advance with the correct answer label of the abnormal state, and generates the machine learning models (1 to N) 17 corresponding to the respective occupants. Since the specific content of the learning process performed by the learning device is similar to the specific content of the learning process performed by the learning device in the first embodiment, redundant description will be omitted.

The threshold setting unit 14*a* sets an abnormal-state determination threshold for estimating the abnormal state of the occupant as in the threshold setting unit 14 of the driver availability detection device 1 according to the first embodiment. Note, however, that the content of the abnormal-state determination threshold set by the threshold setting unit 14*a* and the specific method of setting the abnormal-state determination threshold performed by the threshold setting unit 14*a* are different from the content of the abnormal-state determination threshold set by the threshold setting unit 14 of the driver availability detection device 1 according to the first embodiment and the specific method of setting the abnormal-state determination threshold performed by the threshold setting unit 14, and thus, the following description will be given.

In the second embodiment, the threshold setting unit 14*a* performs "model-specific threshold setting process" and then performs "abnormal-state determination threshold setting process", thereby setting the abnormal-state determination threshold. The threshold setting unit 14*a* performs "model-specific threshold setting process" and "abnormal-state determination threshold setting process" under the control of a control unit.

Specifically, the control unit first causes the threshold setting unit 14*a* to perform "model-specific threshold setting process". The threshold setting unit 14*a* performs "model-specific threshold setting process", and sets a threshold (hereinafter, referred to as "model-specific threshold") used when setting the abnormal state determination threshold for each of the machine learning models (1 to N) 17. Details of "model-specific threshold setting process" will be described later.

When the control unit determines that "model-specific threshold setting process" has been performed, the control unit causes the threshold setting unit 14*a* to perform "abnormal-state determination threshold setting process". The threshold setting unit 14*a* performs "abnormal-state determination threshold setting process" and sets the abnormal-state determination threshold. Details of "abnormal-state determination threshold setting process" will be described later.

Hereinafter, "model-specific threshold setting process" and "abnormal-state determination threshold setting process" performed by the threshold setting unit 14*a* will be described in detail.

"Model-specific threshold setting process" performed by the threshold setting unit 14*a* will be described first.

In the threshold setting unit 14*a*, the model-specific threshold setting unit 141 of the threshold setting unit 14*a* sets a model-specific threshold for each of the machine learning models (1 to N) 17 on the basis of the abnormal state score obtained by inputting the feature amount calculated by the feature-amount calculation unit 13 within the first threshold setting time. Since the first threshold setting time has been described in the first embodiment, redundant description will be omitted. Note, however, that the first threshold setting time in the second embodiment may be the same in length as or different in length from the first threshold setting time in the first embodiment.

Specifically, the model-specific threshold setting unit 141 first inputs the feature amount calculated by the feature-amount calculation unit 13 to a certain machine learning model (1 to N) 17 of the machine learning models (1 to N) 17, and acquires the abnormal state score. The model-specific threshold setting unit 141 performs the acquisition of the abnormal state score for all the machine learning models (1 to N) 17 as described above, and acquires the abnormal state score corresponding to each of the machine learning models (1 to N) 17. The model-specific threshold setting unit 141 generates information (hereinafter referred to as "first score information") in which the acquired abnormal state score corresponding to each of the machine learning models (1 to N) 17, information that can specify the machine learning models (1 to N) 17, and the acquisition date and time of the abnormal state score are associated, and stores the information in the storage unit. The model-specific threshold setting unit 141 acquires and stores the abnormal state score for the first threshold setting time.

Then, when the first threshold setting time elapses, the model-specific threshold setting unit 141 sets, with respect to a certain machine learning model (1 to N) 17 among the machine learning models (1 to N) 17, the maximum value among one or more abnormal state scores stored in the storage unit during the first threshold setting time as the model-specific threshold. The model-specific threshold setting unit 141 is only required to specify, from the first score information, one or more abnormal state scores of the certain machine learning model (1 to N) 17 stored in the storage unit during the first threshold setting time. At this time, the model-specific threshold setting unit 141 may set the model-specific threshold by providing a buffer to the maximum value among one or more abnormal state scores obtained within the first threshold setting time. In addition, the model-specific threshold setting unit 141 may set, as the model-specific threshold, a value obtained by multiplying the maximum value among one or more abnormal state scores obtained within the first threshold setting time by a coefficient. The model-specific threshold setting unit 141 performs the setting of the model-specific threshold for all the machine learning models (1 to N) 17 as described above, and sets the model-specific threshold corresponding to each of the machine learning models (1 to N) 17. The model-specific threshold setting unit 141 generates information (hereinafter referred to as "model-specific threshold information") in which the set model-specific threshold of each of the machine learning models (1 to N) 17 is associated with information that can specify the machine learning model (1 to N) 17, and stores the model-specific threshold information in the storage unit.

When the model-specific threshold setting unit 141 generates the model-specific threshold information corresponding to all the machine learning models (1 to N) 17 and stores the model-specific threshold information in the storage unit, the control unit determines that the "model-specific threshold setting process" is completed.

Next, "abnormal-state determination threshold setting process" performed by the threshold setting unit 14*a* will be described.

In "abnormal-state determination threshold setting process", the threshold setting unit 14*a* sets, for each of the machine learning models (1 to N) 17, an abnormal-state determination threshold for estimating the abnormal state of the occupant on the basis of an abnormal state score obtained by inputting the feature amount related to the occupant calculated by the feature-amount calculation unit 13 within a predetermined time (hereinafter referred to as "second threshold setting time").

In the second embodiment, the second threshold setting time is a time that is set in order to perform a process of setting the abnormal-state determination threshold as a process before the abnormal suite of the occupant is estimated and in which it is assumed that the occupant is in a normal state, similarly to the first threshold setting time. It is assumed that the second threshold setting time is a time after the first threshold setting time elapses. The length of the second threshold setting time is appropriately set to five minutes, ten minutes, or the like. The length of the second threshold setting time may be equal to the length of the first threshold setting time.

First, in the threshold setting unit 14*a*, the model-specific determination unit 142 of the threshold setting unit 14*a* determines, for earth of the machine learning models (1 to N) 17, whether or not the abnormal state score obtained by inputting the feature amount calculated by the feature-amount calculation unit 13 within the second threshold setting time is larger than the model-specific threshold set by the model-specific threshold setting unit 141. Note that the model-specific determination unit 142 can specify the model-specific threshold corresponding to each of the machine learning models (1 to N) 17 from the model-specific threshold information stored in the storage unit by the model-specific threshold setting unit 141.

Specifically, the model-specific determination unit 142 first inputs the feature amount calculated by the feature-amount calculation unit 13 to a certain machine learning model (1 to N) 17 of the machine learning models (1 to N) 17, and acquires the abnormal state score. The model-specific determination unit 142 performs the acquisition of the abnormal state score for all the machine learning models (1 to N) 17 as described above, and acquires the abnormal state score corresponding to each of the machine learning models (1 to N) 17. The model-specific determination unit 142 generates information (hereinafter referred to as "second score information") in which the acquired abnormal state score corresponding to each of the machine learning models (1 to N) 17, information that can specify the machine learning model (1 to N) 17, and the acquisition date and time of the abnormal state score are associated, and stores the determination threshold setting score information in the storage unit. The model-specific determination unit 142 acquires and stores the abnormal state score for the second threshold setting time.

Then, when the second threshold setting time elapses, the model-specific determination unit 142 determines whether or not a certain machine learning model (1 to N) 17 of the machine learning models (1 to N) 17 corresponds to the machine learning model (1 to N) 17 in which any of one or more abnormal state scores stored in the storage unit within the second threshold setting time and obtained from the certain machine learning model (1 to N) 17 is larger than the model-specific threshold set by the model-specific threshold setting unit 141. Hereinafter, the machine learning model (1 to N) 17 in which any of the one or more abnormal state scores obtained from the machine learning model (1 to N) 17 is larger than the model-specific threshold set by the model-specific threshold setting unit 141 is referred to as "count target model".

The model-specific determination unit 142 can specify, from the second score information, one or more abnormal state scores that are obtained from the certain machine learning model (1 to N) 17 and stored in the storage unit during the second threshold setting time.

The model-specific determination unit 142 determines whether or not a certain machine learning model (1 to N) 17 corresponds to "count target model". Specifically, in a case where at least one of the one or more abnormal state scores obtained from the certain machine learning model (1 to N) 17 is larger than the model-specific threshold, the model-specific determination unit 142 determines that the certain machine learning model (1 to N) 17 corresponds to "count target model". Note that, here, the model-specific determination unit 142 determines that the machine learning model (1 to N) 17 corresponds to the count target model in a case where at least one of the one or more abnormal state scores of the machine learning model (1 to N) 17 is larger than the model-specific threshold, but this is merely an example. For example, in a case where the number of abnormal state scores larger than the model-specific threshold among one or more abnormal state scores of the machine learning model (1 to N) 17 is larger than or equal to a predetermined threshold, the model-specific determination unit 142 can determine that the machine learning model (1 to N) 17 corresponds to the count target model.

The model-specific determination unit 142 determines whether or not each of all the machine learning models (1 to N) 17 corresponds to "count target model".

The model-specific determination unit 142 generates, for each of the machine learning models (1 to N) 17, information (hereinafter referred to as "model-specific count-necessity determination result information") in which the determination result as to whether or not the machine learning model (1 to N) 17 corresponds to the count target model and information that can specify the machine learning model (1 to N) 17 are associated with each other, and outputs the model-specific count-necessity determination result information to the threshold setting unit 14a.

The threshold setting unit 14a sets the number of count target models as the abnormal-state determination threshold on the basis of the model-specific count-necessity determination result information output from the model-specific determination unit 142. At this time, the threshold setting unit 14a may set the abnormal-state determination threshold by providing a buffer to the number of count target models. Specifically, the threshold setting unit 14a may set the number of count target models+α as the abnormal-state determination threshold. α is assumed to be larger than 0.

The threshold setting unit 14a stores the set abnormal-state determination threshold in the storage unit in association with the personal identification information output from the authentication unit 12, and sets an estimatable flag to "1".

In the second embodiment, the abnormal state score is output from the machine learning model (1 to N) 17 for the first threshold setting time and the second threshold setting time during which the threshold setting unit 14a performs the process of setting the abnormal-state determination threshold. However, during this time, the driver availability detection device 1a does not estimate the abnormal state of the occupant on the basis of the abnormal state score. For example, the driver availability detection device 1a determines whether to estimate the abnormal state of the occupant on the basis of whether the estimatable flag is "1" or "0". In a case where the estimatable flag is "1", the driver availability detection device 1a determines to estimate the abnormal state of the occupant. On the other hand, in to case where the estimatable flag is "0", the driver availability detection device 1a determines not to estimate the abnormal state of the occupant. The control based on the estimatable flag is executed by the control unit. Since the control based on the estimatable flag by the control unit has been described in the first embodiment, redundant description will be omitted. In the driver availability detection device 1a, the threshold setting unit 14a performs "model-specific threshold setting process" and "abnormal-state determination threshold setting process" in accordance with the control based on the estimatable flag by the control unit. In a case where the model-specific threshold is not set, the control unit causes the threshold setting unit 14a to perform "model-specific threshold setting process". In a case where the model-specific threshold is set and the estimatable flag is "0", the control unit causes the threshold setting unit 14a to perform "abnormal-state determination threshold setting process". Note that since "model-specific threshold setting process" is performed before "abnormal-state determination threshold setting process", the estimatable flag is "0" at the time of performing "model-specific threshold setting process".

Furthermore, in the driver availability detection device 1a, the estimation unit 15a to be described later performs a process of estimating the abnormal state of the occupant in accordance with control based on the estimatable flag executed by the control unit. In a state where the estimatable flag is "1", the control unit causes the estimation unit 15a to perform the process of estimating the abnormal state of the occupant.

The estimation unit 15a estimates the abnormal state of the occupant similarly to the estimation unit 15 of the driver availability detection device 1 according to the first embodiment. Note, however, that since a specific method of estimating the abnormal state of the occupant in the estimation unit 15a is different from that in the estimation unit 15 of the driver availability detection device 1 according to the first embodiment, the following description will be given.

In the second embodiment, the estimation unit 15a estimates the abnormal state of the occupant on the basis of the abnormal state score obtained by inputting the feature amount related to the occupant calculated by the feature-amount calculation unit 13 to each machine learning model (1 to N) 17.

The estimation unit 15a will be described in detail below.

In the estimation unit 15a, the number-of-models calculation unit 151 of the estimation unit 15a calculates the number of machine learning models (hereinafter, "number of abnormality determination models") determined that the abnormal state score obtained by inputting the feature amount calculated by the feature-amount calculation unit 13 is larger than the model-specific threshold among the machine learning models (1 to N) 17.

Specifically, the number-of-models calculation unit 151 first inputs the feature amount calculated by the feature-amount calculation unit 13 to a certain machine learning model (1 to N) 17 of the machine learning models (1 to N) 17, and acquires the abnormal state score. The number-of-models calculation unit 151 then determines whether or not the acquired abnormal state score is larger than the model-specific threshold set by the model-specific threshold setting unit 141 of the threshold setting unit 14a. Note that the number-of-models calculation unit 151 can specify the model-specific threshold corresponding to a certain machine learning model (1 to N) 17 to be compared with the abnormal state score from the model-specific threshold information stored in the storage unit.

The number-of-models calculation unit 151 determines whether or not the abnormal state score is larger than the model-specific threshold for all the machine learning models (1 to N) 17. The number-of-models calculation unit 151 then calculates the number of abnormality determination models.

The number-of-models calculation unit 151 outputs the calculated number of abnormality determination models to the estimation unit 15a.

The estimation unit 15a estimates that the occupant is in the abnormal state in a case where the number of abnormality determination models calculated by the number-of-models calculation unit 151 is larger than the abnormal-state determination threshold set by the threshold setting unit 14a.

Specifically, the estimation unit 15a compares the number of abnormality determination models calculated by the number-of-models calculation unit 151 with the abnormal-state determination threshold stored in the storage unit by the threshold setting unit 14a. At this time, the estimation unit 15a compare the personal identification information output from the authentication unit 12 with the personal identification information associated with the abnormal-state determination threshold in the storage unit, and acquires the abnormal-state determination threshold associated with the matched personal identification information from the storage unit as the abnormal-state determination threshold to be compared with the number of abnormality determination models. In a case where the number of abnormality determination models is larger than the abnormal-state determination threshold, the estimation unit 15a estimates that the occupant is in the abnormal state. On the other hand, in a case where the number of abnormality determination models is less than or equal to the abnormal-state determination threshold, the estimation unit 15a estimates that the occupant is in the normal state.

An operation of the driver availability detection device 1a according to the second embodiment will be described.

Figure 10:
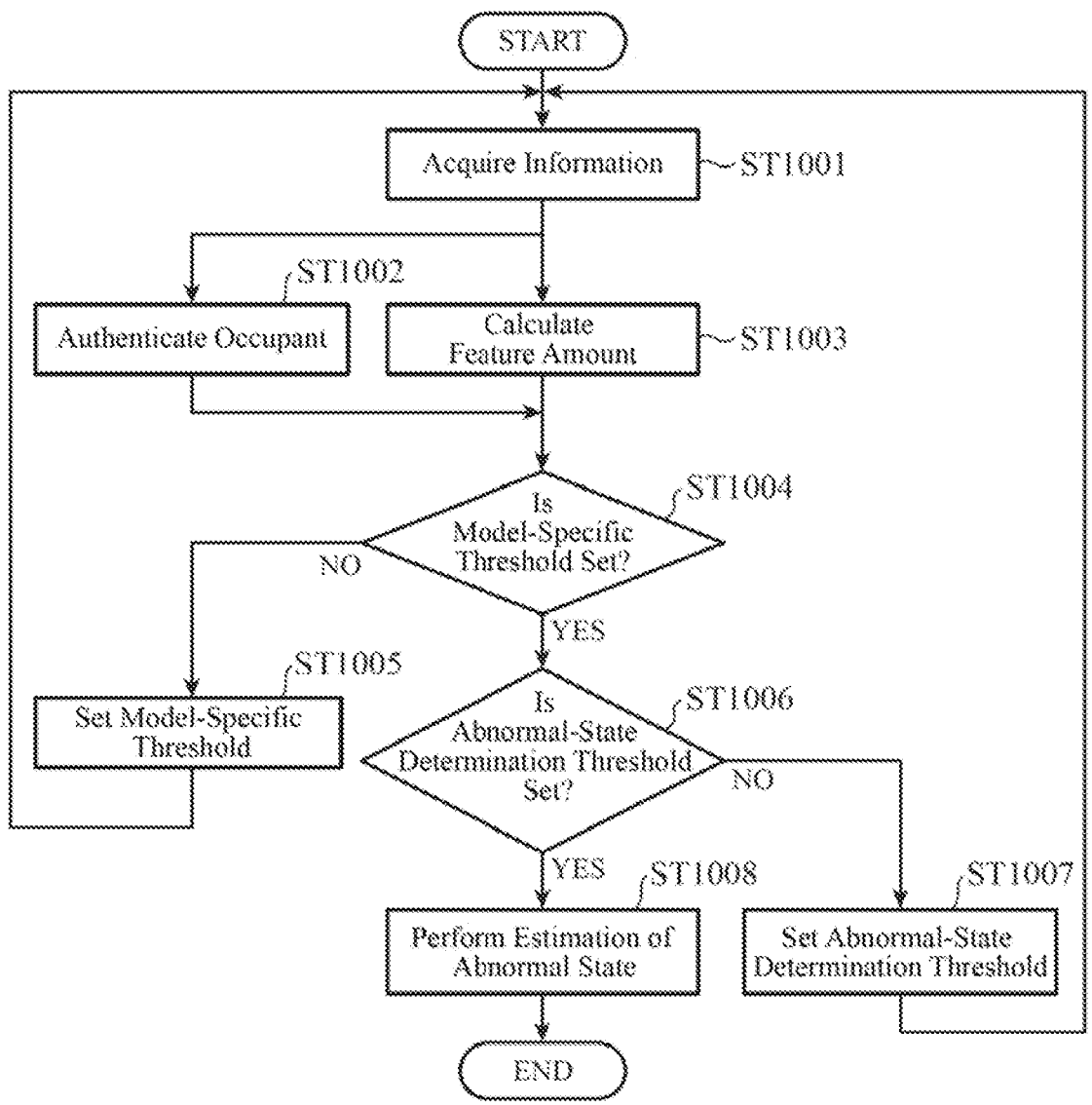
FIG. 10 as flowchart for explaining an operation of the driver availability detection device according to the second embodiment.

FIG. 10 is a flowchart for explaining the operation of the driver availability detection device 1a according to the second embodiment.

The specific operations in steps ST1001 to ST1003 in FIG. 10 are similar to the specific operations in steps ST301 to ST303 in FIG. 3 described in the first embodiment, and thus redundant description will be omitted.

In step ST1004, the control unit determines whether or not the model-specific threshold is set (step ST1004). Specifically, the control unit determines whether or not the model-specific threshold information corresponding to all the machine learning models (1 to N) 17 is stored in the storage unit.

Figure 11:
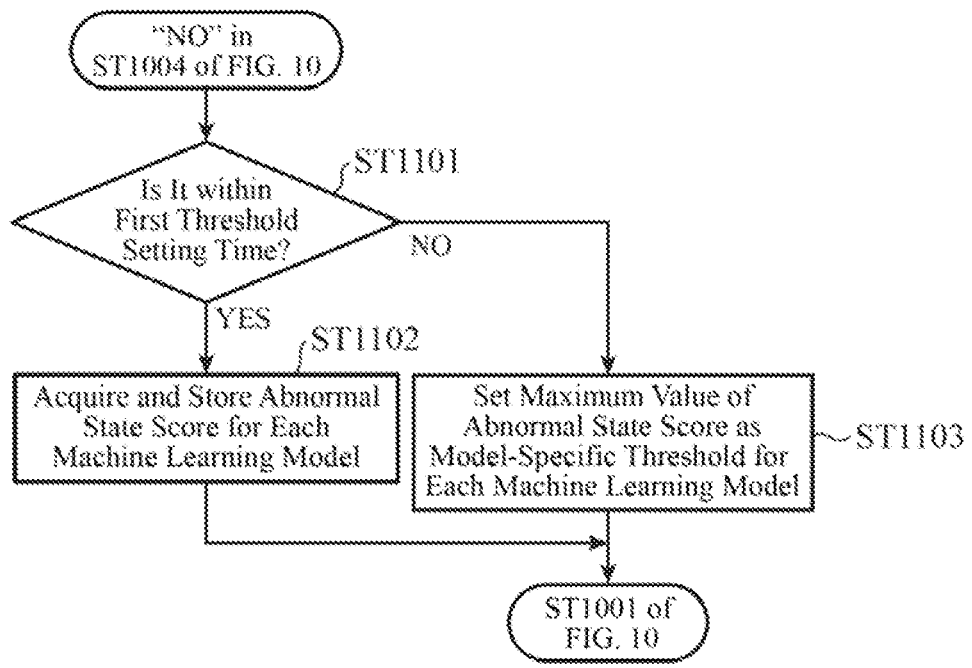
FIG. 11 is a flowchart for explaining a specific operation of step ST1005 in FIG. 10.

If it is determined in step ST1004 that the model-specific threshold is not set ("NO" in step ST1004), the operation of the flowchart in FIG. 10 proceeds to step ST1005. Note that since the model-specific threshold is not set before the operation to be described later with reference to FIG. 11 is performed, the control unit determines that the model-specific threshold is not set. Since the model-specific threshold has been set after the operation to be described later with reference to FIG. 11 is performed, the control unit determines that the model-specific threshold is set.

The threshold setting unit 14a performs "model-specific threshold setting process" (step ST1005).

Here, FIG. 11 is a flowchart for explaining a specific operation of ST1005 in FIG. 10.

The model-specific threshold setting unit 141 determines whether or not it is within the first threshold setting time (step ST1101).

If the model-specific threshold setting unit 141 determines in step ST1101 that it is within the first threshold setting time ("YES" in step ST1101), the model-specific threshold setting unit 141 acquires the abnormal state score by inputting the feature amount most recently calculated in step ST1003 of FIG. 10 by the feature-amount calculation unit 13 to a certain machine learning model (1 to N) 17 of the machine learning models (1 to N) 17. The model-specific threshold setting unit 141 performs the acquisition of the abnormal state score for all the machine learning models (1 to N) 17 as described above, and acquires the abnormal state score corresponding to each of the machine learning models (1 to N) 17. The model-specific threshold setting unit 141 generates first score information and stores the first score information in the storage unit (step ST1102). Thereafter, the operation of the flowchart of FIG. 11 returns to step ST1001 of FIG. 10, and when the operation of step ST1001 is performed, the process proceeds to the operation of steps subsequent to step ST1001 again. The model-specific threshold setting unit 141 performs the operation of step ST1102 thereafter until the first threshold setting time elapses ("NO" in step ST1101). As a result, the first score information generated within the first threshold setting time by the model-specific threshold setting unit 141 is stored in the storage unit.

If the model-specific threshold setting unit 141 determines in step ST1101 that it is not within the first threshold setting time, that is, if the first threshold setting time elapses ("NO" in step ST1101), the model-specific threshold setting unit 141 sets, with respect to a certain machine learning model (1 to N) 17 of the machine learning models (1 to N) 17, the maximum value of one or more abnormal state scores stored in the storage unit within the first threshold setting time as the model-specific threshold (step ST1103). The model-specific threshold setting unit 141 performs the setting of the model-specific threshold for all the machine learning models (1 to N) 17 as described above, and sets the model-specific threshold corresponding to each of the machine learning models (1 to N) 17. The model-specific threshold setting unit 141 generates model-specific threshold information, and stores the model-specific threshold information in the storage unit. Thereafter, the operation of the flowchart of FIG. 11 returns to step ST1001 of FIG. 10, and when the operation of step ST1001 is performed the process proceeds to the operation of steps subsequent to step ST1001 again.

The description returns to the flowchart of FIG. 10.

If the control unit determines in step ST1004 that the model-specific threshold is set ("YES" in step ST1004), the operation of the flowchart in FIG. 10 proceeds to step ST1006.

In step ST1006, the control unit determines whether or not the abnormal-state determination threshold is set. Specifically, the control unit determines whether or not the estimatable flag is "1" (step ST1006).

Figure 12:
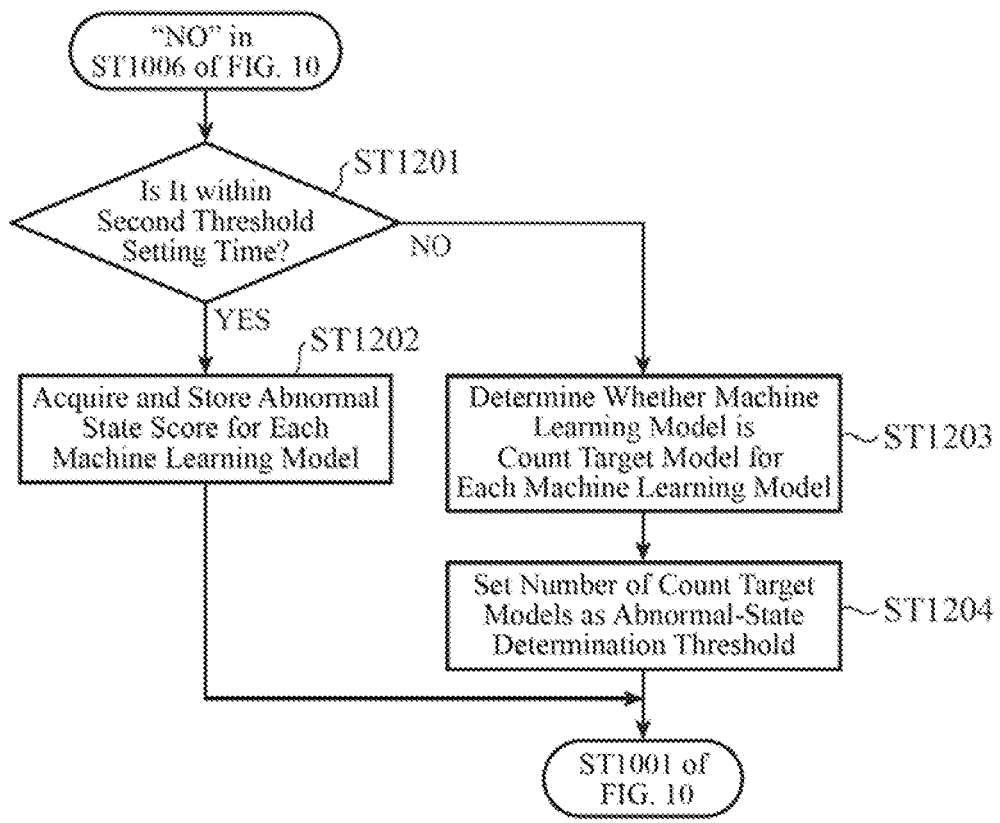
FIG. 12 is a flowchart for explaining a specific operation of step ST1007 in FIG. 10.

If the control unit determines in step ST1006 that the abnormal-state determination threshold is not set, in other words, if the control unit determines that the estimatable flag is "0" ("NO" in step ST1006), the operation of the flowchart of FIG. 10 proceeds to step ST1007. Note that since the abnormal-state determination threshold is not set before the operation to be described later with reference to FIG. 12 is performed, the control unit determines that the abnormal-state determination threshold is not set. Since the abnormal-state determination threshold has been set after the operation to be described later with reference to FIG. 12 is performed, the control unit determines that the abnormal-state determination threshold is set.

The threshold setting unit 14*a* performs "abnormal-state determination threshold setting process" (step ST1007).

Here, FIG. 12 is a flowchart for explaining a specific operation of step ST1007 in FIG. 10.

The model-specific determination unit 142 of the threshold setting unit 14*a* determines whether or not it is within the second threshold setting time (step ST1201).

If the model-specific determination unit 142 determines in step ST1201 that it is within the second threshold setting time ("YES" in step ST1201), the model-specific determination unit 142 acquires the abnormal state score by inputting the feature amount most recently calculated in step ST1003 of FIG. 10 by the feature-amount calculation unit 13 to a certain machine learning model (1 to N) 17 of the machine learning models (1 to N) 17. The model-specific determination unit 142 performs the acquisition of the abnormal state score for all the machine learning models (1 to N) 17 as described above, and acquires the abnormal state score corresponding to each of the machine learning models (1 to N) 17. The model-specific determination unit 142 generates second score information and stores the second store information in the storage unit (step ST1202). Thereafter, the operation of the flowchart of FIG. 12 returns to step ST1001 of FIG. 10, and when the operation of step ST1001 is performed, the process proceeds to the operation of steps subsequent to step ST1001 again. The model-specific determination unit 142 performs the operation of step ST1202 thereafter until the second threshold setting time elapses ("NO" in step ST1201). As a result, the second score information generated within the second threshold setting time by the model-specific determination unit 142 is stored in the storage unit.

If the model-specific determination unit 142 determines in step ST1201 that it is not within the second threshold setting time, that is, if the second threshold setting time elapses ("NO" in step ST1201), the model-specific determination unit 142 determines whether or not any of one or more abnormal state scores of a certain machine learning model (1 to N) 17 of the machine learning models (1 to N) 17, the abnormal state scores being stored in the storage unit within the second threshold setting time, is larger than the model-specific threshold set in step ST1103 of FIG. 11 by the model-specific threshold setting unit 141.

In a case where a certain machine learning model (1 to N) 17 is a machine learning model (1 to N) 17 in which at least one of the one or more abnormal state scores obtained from the certain machine learning model (1 to N) 17 is larger than the model-specific threshold, the model-specific determination unit 142 determines the certain machine learning model (1 to N) 17 as the machine learning model (1 to N) 17 corresponding to the count target model (step ST1203). The model-specific determination unit 142 determines whether or not each of all the machine learning models (1 to N) 17 corresponds to "count target model".

The model-specific determination unit 142 generates model-specific count-necessity determination result information, and outputs the model-specific count-necessity determination result information to the threshold setting unit 14*a*.

The threshold setting unit 14*a* sets the number of count target models as the abnormal-state determination threshold on the basis of the model-specific count-necessity determination result information output from the model-specific determination unit 142 in step ST1203 (step ST1204).

The threshold setting unit 14*a* stores the set abnormal-state determination threshold in the storage unit in association with the personal identification information output from the authentication unit 12, and sets the estimatable flag to "1". Thereafter, the operation of the flowchart of FIG. 12 returns to step ST1001 of FIG. 10, and when the operation of step ST1001 is performed, the process proceeds to the operation of steps subsequent to step ST1001 again.

The description returns to the flowchart of FIG. 10.

If the control unit determines in step ST1006 that the abnormal-state determination threshold is set, in other words, if the control unit determines that the estimatable flag is "1" ("YES" in step ST1006), the operation of the flowchart of FIG. 10 proceeds to step ST1008.

The estimation unit 15*a* then estimates the abnormal state of the occupant on the basis of the abnormal state score obtained by inputting the feature amount related to the occupant calculated in step ST1003 by the feature-amount calculation unit 13 to each of the machine learning models (1 to N) 17 (step ST1008).

Figure 13:
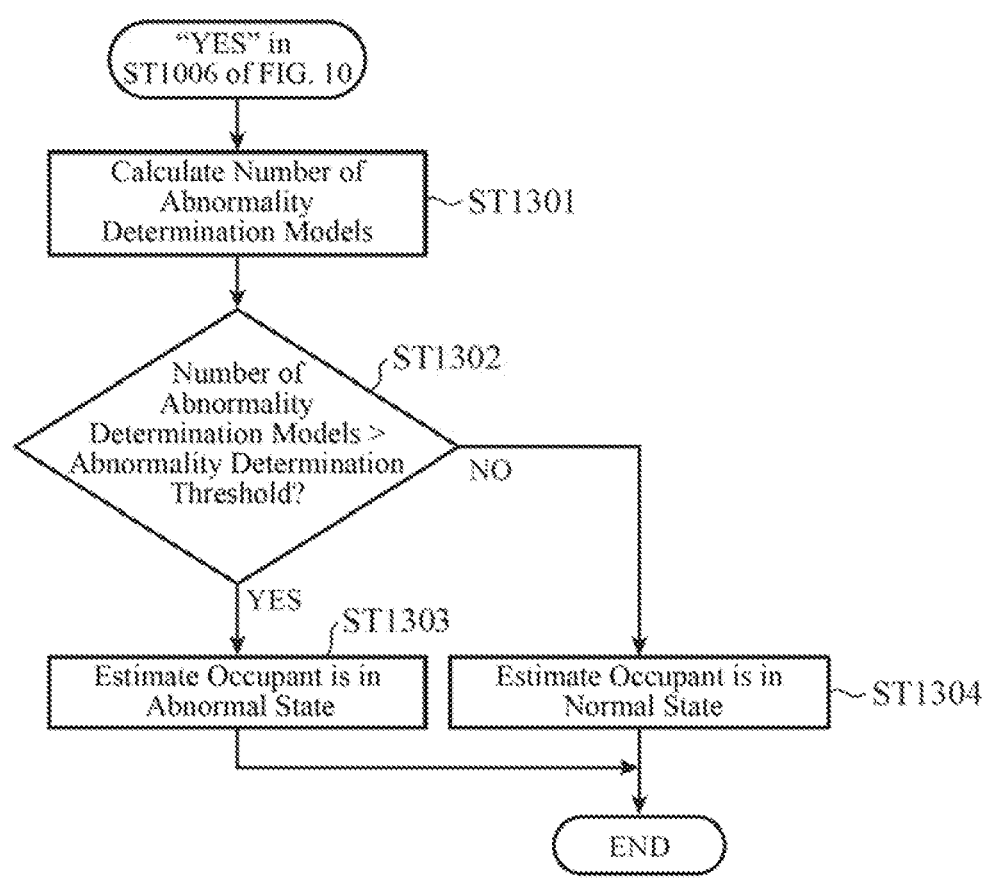
FIG. 13 is a flowchart for explaining a specific operation of step ST1008 in FIG. 10.

Here, FIG. 13 is a flowchart for explaining a specific operation of step ST1008 in FIG. 10.

The number-of-models calculation unit 151 of the estimation unit 15*a* first inputs the feature amount most recently calculated in step ST1003 of FIG. 10 by the feature-amount calculation unit 13 to a certain machine learning model (1 to N) 17 of the machine learning models (1 to N) 17, and acquires the abnormal state score. The number-of-models calculation unit 151 then determines whether or not the acquired abnormal state score is larger than the model-specific threshold set in step ST1103 of FIG. 11 by the model-specific threshold setting unit 141.

The number-of-models calculation unit 151 determines whether or not the abnormal state score is larger than the model-specific threshold for all the machine learning models (1 to N) 17. The number-of-models calculation unit 151 then calculates the number of abnormality determination models (step ST1301).

The number-of-models calculation unit 154 outputs the calculated number of abnormality determination models to the estimation unit 15a.

The estimation unit 15a compares the number of abnormality determination models calculated in step ST1301 by the number-of-models calculation unit 151 with the abnormal-state determination threshold set in step ST1204 of FIG. 12 by the threshold setting unit 14a (step ST1302).

If it is determined in step ST1302 that the number of abnormality determination models is larger than the abnormal-state determination threshold ("YES" in step ST1302), the estimation unit 15a determines that the occupant is in the abnormal state (step ST1303).

On the other hand, if it is determined in step ST1302 that the number of abnormality determination models is less than or equal to the abnormal-state determination threshold ("NO" in step ST1302), the estimation unit 15a determines that the occupant is in the normal state (step ST1304).

Note that in the above description of the operation, the threshold setting unit 14a performs the operation described in the flowchart of FIG. 12 and sets the abnormal-state determination threshold in "abnormal-state determination threshold setting process". However, this is merely an example. For example, the threshold setting unit 14a may set the abnormal-state determination threshold by performing an operation as described below.

In a case where it is within the second threshold setting time, the model-specific determination unit 142 of the threshold setting unit 14a inputs the feature amount most recently calculated in step ST1003 of FIG. 10 by the feature-amount calculation unit 13 to a certain machine learning model (1 to N) 17 of the machine learning models (1 to N) 17, and acquires the abnormal state score. Subsequently, the model-specific determination unit 142 determines whether or not the certain machine learning model (1 to N) 17 corresponds to a count target model by determining whether or not the acquired abnormal state score is larger than the model-specific threshold set in step ST1103 of FIG. 11 by the model-specific threshold setting unit 141. In a case where the abnormal state score obtained from the certain machine learning model (1 to N) 17 is larger than the model-specific threshold set by the model-specific threshold setting unit 141, the model-specific determination unit 142 determines that the certain machine learning model (1 to N) 17 corresponds to the count target model.

The model-specific determination unit 142 acquires the abnormal state score and determines whether or not the machine learning model corresponds to the count target model for all the machine learning models (1 to N) 17. The model-specific determination unit 142 acquires the abnormal state score and determines whether or not the machine learning model corresponds to the count target model for all the machine learning models (1 to N) 17, and then calculates the number of machine learning models (1 to N) 17 corresponding to the count target model among all the machine learning models (1 to N) 17. The model-specific determination unit 142 stores the calculated number of count target models in the storage unit in association with, for example, the time when the number is calculated.

The model-specific determination unit 142 performs the above operation for the second threshold setting time every time the feature-amount calculation unit 13 calculates the feature amount.

When the second threshold setting time elapses, the threshold setting unit 14a sets the maximum value of the number of count target models calculated by the model-specific determination unit 142 within the second threshold setting time as the abnormal-state determination threshold. At this time, the threshold setting unit 14a may set the abnormal-state determination threshold by providing a buffer to the maximum value of the number of count target models calculated within the second threshold setting time. Specifically, the threshold setting unit 14a may set the maximum value of the number of count target models calculated within the second threshold setting time+$\alpha$ as the abnormal-state determination threshold. $\alpha$ is assumed to be larger than 0.

As described above, the driver availability detection device 1a according to the second embodiment assumes that the occupant is in the normal state for the first threshold setting time, and sets, for each of the machine learning models (1 to N) 17, the model-specific threshold on die basis of the maximum value of the abnormal state score obtained by inputting the feature amount related to the occupant during the first threshold setting time.

Further, after setting the model-specific threshold, the driver availability detection device 1a assumes that tire occupant is in the normal state for the second threshold setting time, compares the abnormal state score obtained by inputting the feature amount related to the occupant during the second threshold setting time with the model-specific threshold for each machine learning model (1 to N) 17, and calculates the number of machine learning models (1 to N) 17 corresponding to the count target model among the machine learning models (1 to N) 17. The driver availability detection device 1a then sets the calculated number of count target models as the abnormal-state determination threshold.

After setting the abnormal-state determination threshold, the driver availability detection device 1a inputs the feature amount related to the occupant for each machine learning model (1 to N) 17, and acquires the abnormal state score for each machine learning model (1 to N) 17. The driver availability detection device 1a determines whether or not each machine learning model (1 to N) 17 is an abnormality determination model in which the obtained abnormal state score is larger than the model-specific threshold. The driver availability detection device 1a then calculates the number of abnormality determination models.

After calculating the number of abnormality determination models, the driver availability detection device 1a compares the number of abnormality determination models with the abnormal-state determination threshold, and estimates that the occupant is in the abnormal state in a case where the number of abnormality determination models is larger than the abnormal-state determination threshold.

The driver availability detection device 1a does not estimate whether or not the occupant is in the abnormal state using a fixed threshold, but sets the abnormal-state determination threshold for each occupant, and estimates whether or not the occupant is in the abnormal state using the abnormal-state determination threshold. Consequently, when estimating whether or not the occupant is in the abnormal state, the driver availability detection device 1a can prevent erroneous estimation of the abnormal state of the occupant.

In addition, the driver availability detection device 1a sets the abnormal-state determination threshold and estimates the abnormal state of the occupant on the basis of a plurality of machine learning models (1 to N) 17 individually generated in advance depending on attributes of a plurality of occupants with various attributes. As a result, the driver availability detection device 1a can improve the accuracy of estimating the abnormal state of the occupant as compared with the case of setting the abnormal-state determination threshold and estimating the abnormal state of the occupant using one machine learning model generated from the information related to the occupants with various attributes.

Note that also in the driver availability detection device 1a according to the second embodiment like the driver availability detection device 1 according to the first embodiment, for example, the estimation unit 15a may estimate that the occupant is in the abnormal state when the rate at which the occupant is estimated to be in the abnormal state is larger than or equal to a threshold during the driver availability detection time, and thereafter, does not have to estimate the abnormal state of the occupant until the driving of the vehicle is ended.

According to the second embodiment, in the driver availability detection device 1a, the information input to the machine learning model (1 to N) 17 is the feature amount related to the occupant calculated by the feature-amount calculation unit 13, but this is merely an example. For example, in the driver availability detection device 1a, the information input to the machine learning model (1 to N) 17 may be information related to the occupant acquired by the information acquisition unit 11. In this case, the driver availability detection device 1a can be configured not to include the feature-amount calculation unit 13.

Note, however, that when the driver availability detection device 1a includes the feature-amount calculation unit 13 and inputs the feature amount related to the occupant, the feature amount having a large correlation with the estimation of the abnormal state, to the machine learning model (1 to N) 17, the accuracy of estimation at the time of estimating the abnormal state of the occupant can be improved as compared with the case where the information related to the occupant is directly input to the machine learning model (1 to N) 17.

Note that, in a case where the information input to the machine learning model (1 to N) 17 is the information related to the occupant in the driver availability detection device 1a, the learning device sets the information related to the occupant as teacher data.

As described above, according to the second embodiment, the driver availability detection device 1a that estimates the abnormal state of the occupant on the basis of the information related to the occupant of the vehicle and the machine learning model (1 to N) 17 includes the information acquisition unit 11 that acquires the information related to the occupant and the threshold setting unit 14a that sets the abnormal-state determination threshold for estimating the abnormal state of the occupant on the basis of the abnormal state score obtained by inputting the information related to the occupant acquired by the information acquisition unit 11 to the machine learning model (1 to N) 17 within the first threshold setting time.

Consequently, when estimating whether or not the occupant is in the abnormal state, the driver availability detection device 1a can prevent erroneous estimation of the abnormal state of the occupant.

In particular, in the second embodiment, there are a plurality of machine learning models (1 to N) 17, and the driver availability detection device 1a includes the model-specific threshold setting unit 141 that sets the model-specific threshold for each of the machine learning models (1 to N) is basis of the abnormal state score obtained by inputting the information related to the occupant acquired by the information acquisition unit 11 within the first threshold setting time, and the model-specific determination unit 142 that determines, after the model-specific threshold setting unit 141 sets the model-specific threshold, whether or not the abnormal state score obtained by inputting the information related to the occupant acquired by the information acquisition unit within the second threshold setting time is larger than the model-specific threshold set by the model-specific threshold setting unit 141 for each of the machine learning models (1 to N) 17, and the threshold setting unit 14a sets the number of the machine learning models (1 to N) 17 in which the model-specific determination unit 142 determines that the abnormal state score is larger the model-specific threshold as the abnormal-state determination threshold.

As a result, the driver availability detection device 1a can improve the accuracy of estimating the abnormal state of the occupant as compared with the case of setting the abnormal-state determination threshold and estimating the abnormal state of the occupant using one machine learning model generated from the information related to occupants with various attributes.

Third Embodiment

In the second embodiment, it is assumed that a plurality of machine learning models (1 to N) 17 are generated in advance on the basis of information related to a plurality or occupants. Note that the machine learning models (1 to N) 17 are generated on the basis of information related to a plurality of occupants with various attributes.

The driver availability detection device 1a then sets the abnormal-state determination threshold and estimates the abnormal state of the occupant using all the generated machine learning models (1 to N) 17.

Here, the abnormal state of the occupant may have a different tendency depending on the attribute of the occupant. For example, there is a case where an occupant belonging to an elderly group is likely to have a difference in a biological feature amount in an abnormal state, whereas there is a case where an occupant belonging to a younger group is likely to have a difference in a facial feature amount in the abnormal state. As a result, for example, the tendency of the abnormal state may be different between the occupant belonging to the elderly group and the occupant belonging to the younger group. In addition, for example, the tendency of the abnormal state may be different between male and female.

Consequently, in a third embodiment, an embodiment will be described in which a driver availability detection device 1b selects one or more machine learning models (hereinafter, referred to as "related machine learning models") related to an attribute of an occupant whose abnormal state is to be estimated among a plurality or machine learning models (1 to N) 17, and sets the abnormal-state determination threshold and estimates the abnormal state of the occupant using the selected one or more related machine learning models.

The driver availability detection device 1b according to the third embodiment is assumed to be mounted on a vehicle similarly to the driver availability detection device 1a according to the second embodiment.

Figure 14:
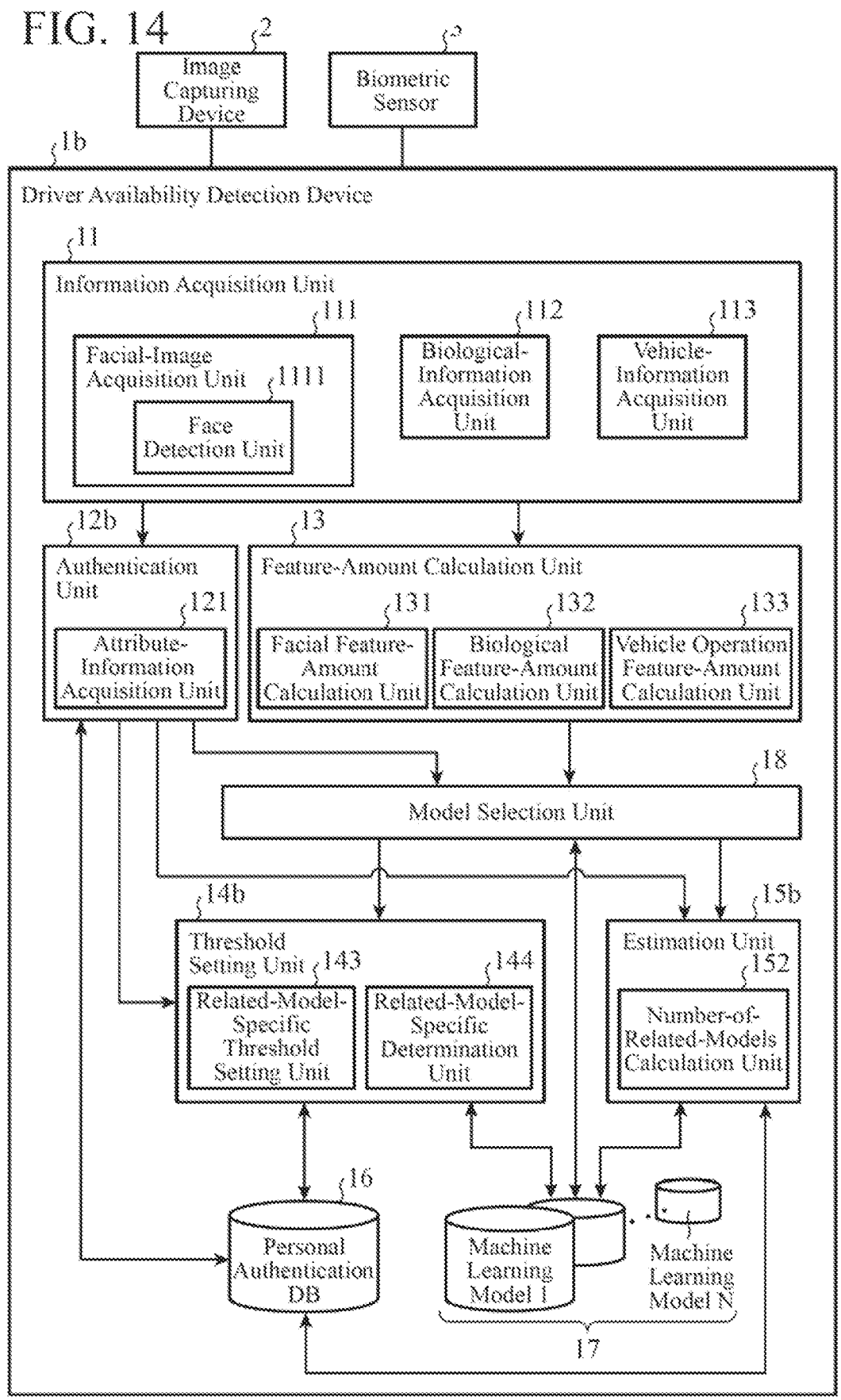
FIG. 14 is a diagram illustrating a configuration example of a driver availability detection device according to a third embodiment.

FIG. 14 is a diagram illustrating a configuration example of the driver availability detection device 1b according to the third embodiment.

In the configuration example of the driver availability detection device 1b according to the third embodiment, the same components as those of the driver availability detection device 1a described in the second embodiment with reference to FIG. 8 are denoted by the same reference numerals, and redundant description will be omitted.

The driver availability detection device 1b according to the third embodiment is different from the driver availability detection device 1a according to the second embodiment in that an authentication unit 12b includes an attribute-information acquisition unit 121.

In addition, the driver availability detection device 1b according to the third embodiment is different from the driver availability detection device 1a according to the second embodiment in that the driver availability detection device 1b includes a model selection unit 18.

Further, the driver availability detection device 1b according to the third embodiment is different from the driver availability detection device 1a according to the second embodiment in that a threshold setting unit 14b includes a related-model-specific threshold setting unit 143 and a related-model-specific determination unit 144 instead of the model-specific threshold setting unit 141 and the model-specific determination unit 142.

Furthermore, the driver availability detection device 1b according to the third embodiment is different from the driver availability detection device 1a according to the second embodiment in that an estimation unit 15b includes a number-of-related-models calculation unit 152 instead of the number-of-models calculation unit 151.

Also in the third embodiment, it is assumed that a plurality of machine learning models (1 to N) 17 are generated in advance as in the second embodiment.

The machine learning models (1 to N) 17 are generated in advance by a learning device as in the second embodiment (see FIG. 9). Note, however, that in the third embodiment, the learning device acquires attribute information related to the attribute of the occupant, and gives the attribute information to the generated machine learning model (1 to N) 17.

The attribute-information acquisition unit 121 of the authentication unit 12b acquires the attribute information related to the attribute of the occupant. The attribute of the occupant is, for example, gender or age.

The authentication unit 12b authenticates the individual occupant and acquires personal identification information. Since a specific method of acquiring the personal identification information by the authentication unit 12b is similar to the specific method of acquiring the personal identification information by the authentication unit 12 described in the first embodiment, redundant description will be omitted.

In the thud embodiment, when the authentication unit 12b acquires the personal identification information, in the authentication unit 12b, the attribute-information acquisition unit 121 acquires the attribute information related to the attribute of the occupant.

Specifically, the attribute-information acquisition unit 121 acquires the attribute information of the occupant from personally identifiable in stored in the personal authentication DB 16. Note that, in the third embodiment, for example, it is assumed that die attribute information is set in the personally identifiable information. This is merely an example, and for example, the attribute-information acquisition unit 121 may receive the attribute information of the occupant input from an input device (not illustrated). Specifically, for example, the occupant uses a navigation device (not illustrated) mounted on the vehicle or a portable terminal carried by the occupant as an input device to input the attribute information of the occupant. The attribute-information acquisition unit 121 may receive the attribute information input by the occupant.

In a case where the individual occupant can be identified, the authentication unit 12b outputs the acquired personal identification information and attribute information of the occupant to the threshold setting unit 14b, the estimation unit 15b, and the model selection unit 18.

The model selection unit 18 selects one or more related machine learning models related to the attribute of the occupant from the machine learning models (1 to N) 17 on the basis of the attribute information acquired by the attribute-information acquisition unit 121 of the authentication unit 12b.

Specifically, the model selection unit 18 compares the attribute information acquired by the attribute-information acquisition unit 121 with the attribute information given to the machine learning models (1 to N) 17, and selects one or more related machine learning models. The model selection unit 18 selects one or more related machine learning models according to a predetermined model selection rule.

For example, it is assumed that the attribute information acquired from the attribute-information acquisition unit 121 is information indicating the age and gender of the occupant, and the occupant is a 60 year-old male. Meanwhile, it is assumed that the attribute information given to the machine learning models (1 to N) 17 is age and gender. Then, it is assumed that "similar age and same gender as occupant" is set in the model selection rule.

In this case, the model selection unit 18 selects the machine learning model (1 to N) 17 to which the attribute information indicating a male in his sixties is given.

In addition, for example, it is assumed that the attribute information acquired from the attribute-information acquisition unit 121 is a date of birth. Meanwhile, it is assumed that the attribute information given to the machine learning models (1 to N) 17 is age. Then, it is assumed that "similar age and same gender as occupant" is set in the model selection rule.

In this case, for example, the model selection unit 18 can calculate the age of the occupant from the date of birth, and select the machine learning model (1 to N) 17 related to the attribute of the occupant from the calculated age.

The model selection unit 18 outputs information of the selected related machine learning model to the threshold setting unit 14b and the estimation unit 15b.

The related machine learning model selected by the model selection unit 18 is used for the setting of the abnormal-state determination threshold in the threshold setting unit 14b and the estimation of the abnormal state in the estimation unit 15b.

As described above, the model selection unit 18 selects one or more related machine learning models from the machine learning models (1 to N) 17. However, if the number of related machine learning models selected by the model selection unit 18 is too small, the threshold setting unit 14b may not be able to appropriately set the abnormal-state determination threshold. As a result, the estimation unit 15b may not be able to appropriately estimate the abnormal state. Consequently, the model selection 18 preferably selects a certain number of related machine learning models set in advance, such as larger than or equal to a hundred.

For example, a plurality of rules to which priority is given may be set in the model selection rule. The model selection unit 18 then selects the related machine learning models according to the rule in descending order of priority in a manner that the number of the related machine learning models is larger than or equal to a predetermined number.

For example, it is assumed that, in the model selection rule, "similar age and same gender as occupant" is set as a rule with a first priority, and "similar age as occupant or five years older or younger than occupant, and same gender as occupant" or "similar age as occupant" is set as a rule with a second priority.

It is assumed that the attribute information acquired from the attribute-information acquisition unit 121 is information indicating the age and gender of the occupant, and the occupant is a 60 year-old male. Furthermore, it is assumed that the attribute information given to the machine learning models (1 to N) 17 is age and gender.

In this case, the model selection unit 18 selects first, as the related machine learning model, the machine learning model (1 to N) 17 to which the attribute information indicating a male in his sixties is given according to the rule with the first priority.

Here, the model selection unit 18 determines whether or not the number of related machine learning models is larger than or equal to a predetermined number.

In a case where the number of related machine learning models is less than the predetermined number, the model selection unit 18 then selects, as the related machine learning model, a machine learning model (1 to N) 17 to which attribute information indicating a male of the age of 55 to 75 years old is given and a machine learning model (1 to N) 17 to which attribute information indicating a female in her sixties is given, in accordance with the rule with the second priority.

When the total of the related machine learning model selected according to the rule with the first priority and the related machine learning model selected according to the rule with the second priority is larger than or equal to a predetermined number, the model selection unit 18 ends the selection of the related machine learning model.

When the total of the related machine learning model selected according to the rule with the first priority and the related machine learning model selected according to the rule with the second priority is less than the predetermined number, the model selection unit 18 continues to select the related machine learning model according to a rule with a third priority.

The description returns to FIG. 14.

The threshold setting unit 14b sets an abnormal-state determination threshold for estimating the abnormal state of the occupant as in the threshold setting unit 14a of the driver availability detection device 1a according to the second embodiment.

The threshold setting unit 14b is different from the threshold setting unit 14a according to the second embodiment in that the machine learning model used in setting the abnormal-state determination threshold is the related machine learning model selected by the model selection unit 18.

The threshold setting unit 14b performs "related-model-specific threshold setting process" and then performs "abnormal-state determination threshold setting process", thereby setting the abnormal-state determination threshold. The threshold setting unit 14b performs "related-model-specific threshold setting process" and "abnormal-state determination threshold setting process" under the control of a control unit.

Specifically, the control unit first causes the threshold setting unit 14b to perform "related-model-specific threshold setting process". The threshold setting unit 14b performs "related-model-specific threshold setting process", and sets a threshold (hereinafter, referred to as "related-model-specific threshold") used when setting the abnormal-state determination threshold for each related machine learning model. Details of "related-model-specific threshold setting process" will be described later.

When determining that "related-model-specific threshold setting process" is performed, the control unit causes the threshold setting unit 14b to perform "abnormal-state determination threshold setting process". The threshold setting unit 14b performs "abnormal-state determination threshold setting process" and sets the abnormal-state determination threshold. Details of "abnormal-state determination threshold setting process" will be described later.

Hereinafter, "related-model-specific threshold setting process" and "abnormal-state determination threshold setting process" performed by the threshold setting unit 14b will be described in detail.

"Related-model-specific threshold setting process" performed by the threshold setting unit 14b will be described first.

In the threshold setting unit 14b, the related-model-specific threshold setting unit 143 of the threshold setting unit 14b sets a related-model-specific threshold for each of one or more related machine learning models selected by the model selection unit 18 on the basis of the abnormal state score obtained by inputting the feature amount calculated by the feature-amount calculation unit 13 within the first threshold setting time. Since the first threshold setting time has been described in the first embodiment, redundant description will be omitted. Note, however, that the first threshold setting time in the third embodiment may be the same in length as or different in length from the first threshold setting time in the first embodiment.

Specifically, the related-model-specific threshold setting unit 143 first inputs the feature amount calculated by the feature-amount calculation unit 13 to a certain related machine learning model of one or more related machine learning models, and acquires the abnormal state score. The related-model-specific threshold selling unit 143 performs the acquisition of the abnormal state score for all the related machine learning models as described above, and acquires the abnormal state score corresponding to each of the related machine learning models. The related-model-specific threshold setting unit 143 generates information (hereinafter referred to as "third score information") in which the acquired abnormal state score corresponding to each related machine learning model, information that can specify the related machine learning model, and the acquisition date and time of the abnormal state score are associated, and stores the third score information in the storage unit. The related-model-specific threshold setting unit 143 acquires and stores the abnormal state score for the first threshold setting time.

Then, when the first threshold setting time elapses, the related-model-specific threshold setting unit 143 sets, with respect to a certain related machine learning model of one or more related machine learning models, the maximum value among one or more abnormal state scores stored in the storage unit during the first threshold setting time as the related-model-specific threshold. The related-model-specific threshold setting unit 143 can specify, from the third score information, one or more abnormal state scores of the certain related machine learning model stored in the storage unit during the first threshold setting time. At this time, the related-model-specific threshold setting unit 143 may set the related-model-specific threshold by providing a buffer to the maximum value among one or more abnormal state scores obtained within the first threshold setting time. In addition the related-model-specific threshold setting unit 143 may set, as the related-model-specific threshold, a value obtained by multiplying the maximum value among one or more abnormal state scores obtained within the first threshold setting time by a coefficient. The related-model-specific threshold setting unit 143 performs the setting of the related-model-specific threshold for all the related machine learning models is described above, and sets the related-modelspecific threshold score corresponding to each of the related machine learning models. The related-model-specific threshold setting unit 143 generates information (hereinafter referred to as "related-model-specific threshold information") in which the set related-model-specific threshold corresponding to each of the related machine learning models is associated with information that can specify the related machine learning model, and stores the related-model-specific threshold information in the storage unit.

When the related-model-specific threshold setting unit 143 generates the related-model-specific threshold information and stores the related-model-specific threshold information in the storage unit, the control unit determines that "related-model-specific threshold setting process" is completed.

Next, "abnormal-state determination threshold setting process" performed by the threshold setting unit 14b will be described.

In "abnormal-state determination threshold setting process", the threshold setting unit 14b sets, for each of one or more related machine learning models, the abnormal-state determination threshold for estimating the abnormal state of the occupant on the basis of the abnormal state score obtained by inputting the feature amount related to the occupant calculated by the feature-amount calculation unit 13 within a predetermined time (hereinafter referred to as "third threshold setting time").

In the third embodiment, the third threshold setting time is a time that is set in order to perform a process of setting the abnormal-state determination threshold as a process before the abnormal state of the occupant is estimated and in which it is assumed that the occupant is in the normal state, similarly to the first threshold setting time. It is assumed that the third threshold setting time is a time after the lint threshold setting time elapses. The length of the third threshold setting time is appropriately set to five minutes, ten minutes, or the like. The length of the third threshold setting time may be equal to the length of the first threshold setting time. The length of the third threshold setting time may be equal to the length of the second threshold setting time described in the second embodiment.

First, in the threshold setting unit 14b, the related-model-specific determination unit 144 of the threshold setting unit 14b determines, for each of one or more related machine learning models, whether or not the abnormal state score obtained by inputting the feature amount calculated by the feature-amount calculation unit 13 within the third threshold setting time is larger than the related-model-specific threshold set by the related-model-specific threshold setting unit 143. Note that the related-model-specific determination unit 144 can specify the related-model-specific threshold corresponding to each of the related machine learning models from the related-model-specific threshold information stored in the storage unit by the related-model-specific threshold setting unit 143.

Specifically, the related-model-specific determination unit 144 first inputs the feature amount calculated by the feature-amount calculation unit 13 to a certain related machine learning model of one or more related machine learning models, and acquires the abnormal state score. The related-model-specific determination unit 144 performs the acquisition of the abnormal state score for all the related machine learning models as described above, and acquires the related abnormal state score corresponding to each of the related machine learning models. The related-model-specific determination unit 144 generates information (hereinafter referred to as "fourth score information") in which the acquired abnormal state score corresponding to each related machine learning model, information that can specify the related machine learning model, and the acquisition date and time of the abnormal state score are associated, and stores the fourth score information in the storage unit. The related-model-specific determination unit 144 acquires and stores the abnormal state score for the third threshold setting time.

Then, when the third threshold setting time elapses, the related-model-specific determination unit 144 determines whether or not a certain related machine learning model of one or more related machine learning models corresponds to a related machine learning model in which any of one or more abnormal state scores stored in the storage unit within the third threshold setting time and obtained from the certain related machine learning model is larger than the related-model-specific threshold set by the related-model-specific threshold setting unit 143. Hereinafter, in the third embodiment, the related machine learning model in which any of one or more abnormal state scores obtained from the related machine learning model is larger than the related-model-specific threshold set by the related-model-specific threshold setting twit 143 is referred to as "count target model".

The related-model-specific determination unit 144 can specify, from the fourth score information, one or more abnormal state scores that are obtained from the certain related machine learning model and stored in the storage unit during the third threshold setting time.

The related-model-specific determination unit 144 determines whether or not a certain related machine learning model corresponds to "count target model". Specifically, in a case where at least one of one or more abnormal state scores obtained from the certain related machine learning model is larger than the related-model-specific threshold, the related-model-specific determination unit 144 determines that the certain related machine learning model corresponds to "count target model". Note that, here, with respect to the related machine learning model, the related-model-specific determination unit 144 determines that the related machine learning model corresponds to the count target model in a case where at least one of one or more abnormal state scores is larger than the related-model-specific threshold, but this is merely an example. For example, in a case where the number of abnormal state scores larger than the related-model-specific threshold among one or more related abnormal state scores of the related machine learning model is larger than or equal to a predetermined threshold, the related-model-specific determination unit 144 can determine that the related machine learning model corresponds to the count target model.

The related-model-specific determination unit 144 determines whether or not each of all the related machine learning models corresponds to "count target model".

The related-model-specific determination unit 144 generates, for each of the related machine learning models, information (hereinafter referred to as "related-model-specific count-necessity determination result information") in which the determination result as to whether or not the related machine learning model corresponds to the count target model and information that can specify the related machine learning model are associated with each other, and outputs the related-model-specific count-necessity determination result information to the threshold setting unit 14b.

The threshold setting unit 14b sets the number of count target models as the abnormal-state determination threshold on the basis of the related-model-specific count-necessity determination result information output from the related-model-specific determination unit 144. At this time, the threshold setting unit 14b can set the abnormal-state determination threshold by providing a buffer to the number of count target models. Specifically, the threshold setting unit 14b can set the number of count target models+α as the abnormal-state determination threshold. α is assumed to be larger than 0.

The threshold setting unit 14b stores the set abnormal-state determination threshold in the storage unit in association with the personal identification information output from the authentication unit 12b, and sets an estimatable flag to "1".

In the third embodiment, the abnormal state score is output from the related machine learning model for the first threshold setting time and the third threshold setting time during which the threshold setting unit 14b performs the process of setting the abnormal-state determination threshold. However, during this time, the driver availability detection device 1b does not estimate the abnormal state of the occupant on the basis of the abnormal state score. For example, the driver availability detection device 1b determines whether to estimate the abnormal state of the occupant on the basis of whether the estimatable flag is "1" or "0". In a case where the estimatable flag is "1", the driver availability detection device 1b determines to estimate the abnormal slate of the occupant. On the other hand, in a case where the estimatable flag is "0", the driver availability detection device 1b determines not to estimate the abnormal state of the occupant. The control based on the estimatable flag is executed by the control unit. Since the control based on the estimatable flag by the control unit has been described in the first embodiment, redundant description will be omitted. In the driver availability detection device 1b, the threshold setting unit 14b performs "related-model-specific threshold setting process" and "abnormal-state determination threshold setting process" in accordance with the control based on the estimatable flag by the control unit. In a case where the related-model-specific threshold is not set, the control unit causes the threshold setting unit 14b to perform "related-model-specific threshold setting process". In a case where the related-model-specific threshold is set and the estimatable flag is "0", the control unit causes the threshold setting unit 14b to perform "abnormal-state determination threshold setting process". Note that since "related-model-specific threshold setting process" is performed before "abnormal-state determination threshold setting process", the estimatable flag is "0" at the time of performing "related-model-specific threshold setting process".

Furthermore, in the driver availability detection device 1b, the estimation unit 15b to be described later performs a process of estimating the abnormal state of the occupant in accordance with the control based on the estimatable flag executed by the control unit. In a state where the estimatable flag is "1", the control unit causes the estimation unit 15b to perform the process of estimating the abnormal state of the occupant.

The estimation unit 15b estimates the abnormal state of the occupant similarly to the estimation unit 15a of the driver availability detection device 1a according to the second embodiment.

The estimation unit 15b is different from the estimation unit 15a according to the second embodiment in that the machine learning model used for estimating the abnormal state of the occupant is changed to one or more related machine learning models selected by the model selection unit 18.

The estimation unit 15b estimates the abnormal state of the occupant on the basis of the abnormal state score obtained by inputting the feature amount related to the occupant calculated by the feature-amount calculation unit 13 to one or more related machine learning models selected by the model selection unit 18.

The estimation unit 15b will be described in detail below.

In the estimation unit 15b, the number-of-related-models calculation unit 152 of the estimation unit 15b calculates the number of related machine learning models (hereinafter, "number of abnormality determination related models") determined that the abnormal state score obtained by inputting the feature amount calculated by the feature-amount calculation unit 13 is larger than the related-model-specific threshold among one or more related machine learning models.

Specifically, the number-of-related-models calculation unit 152 first inputs the feature amount calculated by the feature-amount calculation unit 13 to a certain related machine learning model of one or more related machine learning models, and acquires the abnormal state score. Then, the number-of-related-models calculation unit 152 determines whether or not the acquired abnormal state score is larger than the related model-specific threshold set by the related-model-specific threshold setting unit 143 of the threshold setting unit 14b. Note that the number-of-related-models calculation unit 152 can specify the related-model-specific threshold corresponding to a certain related machine learning model to be compared with the abnormal state score from the related-model-specific threshold information stored in the storage unit.

The number-of-related-models calculation unit 152 determines whether or not the abnormal state score is larger than the related-model-specific threshold for all the related machine learning models. The number-of-related-models calculation unit 152 then calculates the number or abnormality determination related models.

The number-of-related-models calculation unit 152 outputs the calculated number of abnormality determination related models to the estimation unit 15b.

The estimation unit 15b estimates that the occupant is in the abnormal state in a case where the number of abnormality determination related models calculated by the number-of-related-models calculation unit 152 is larger than the abnormal-state determination threshold set by the threshold setting unit 14b.

Specifically, the estimation unit 15b compares the number of abnormality determination related models calculated by the number-of-related-models calculation unit 152 with the abnormal-state determination threshold stored in the storage unit by the threshold setting unit 14b. At this time, the estimation unit 15b compares the personal identification information output from the authentication unit 12b with the personal identification information associated with the abnormal-state determination threshold in the storage unit, and acquires the abnormal-state determination threshold associated with the matched personal identification information from the storage unit as the abnormal-state determination threshold to be compared with the number of abnormality determination related models. In a case where the number of abnormality determination related models is larger than the abnormal-state determination threshold, the estimation unit 15b estimates that the occupant is in the abnormal state. On the other hand, in a case where the number of abnormality determination related models is less than or equal to the abnormal-state determination threshold, the estimation unit 15b estimates that the occupant is in the normal state.

An operation of the driver availability detection device 1*b* according to the third embodiment will be described.

Figure 15:
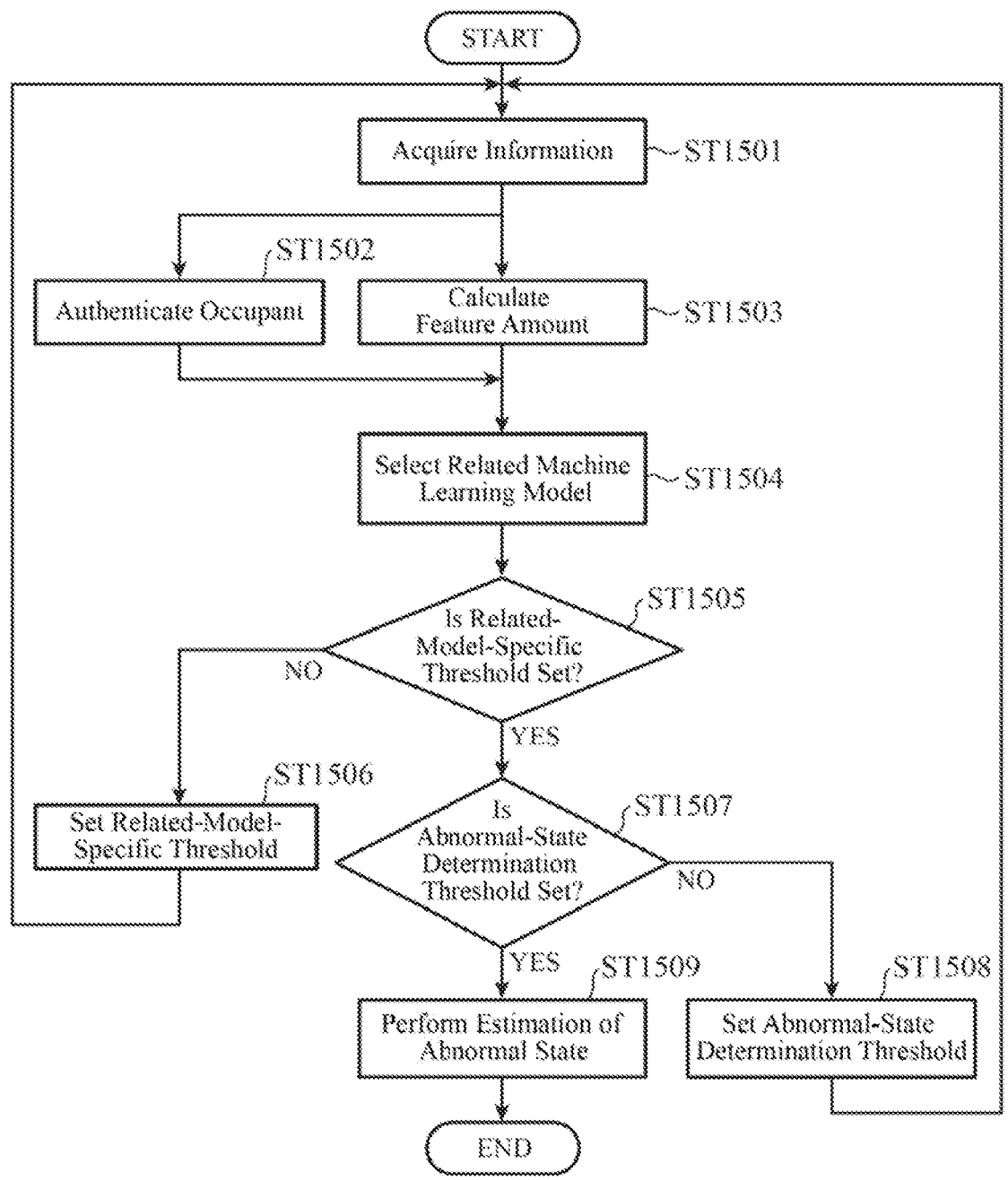
FIG. 15 is a flowchart far explaining an operation of the driver availability detection device according to the third embodiment.

FIG. 15 is a flowchart for explaining the operation of the driver availability detection device 1*b* according to the third embodiment.

The specific operations in steps ST1501 and ST1503 in FIG. 15 are similar to the specific operations in steps ST1001 and ST1003 in FIG. 10 described in the second embodiment, and thus redundant description will be omitted.

In step ST1502, the authentication unit 12*b* authenticates the individual occupant (step ST1502).

When authenticating the individual occupant, the authentication unit 12*b* acquires personal identification information. At this time, the attribute-information acquisition unit 121 of the authentication unit 12*b* acquires the attribute information of the occupant.

In a case where the individual occupant can be identified, the authentication unit 12*b* outputs the acquired personal identification information and attribute information of the occupant to the threshold setting unit 14*b*, the estimation unit 15*b*, and the model selection unit 18.

Note that in a case where the authentication unit 12*b* cannot identify the individual occupant, the driver availability detection device 1*b* ends the operation of the flowchart of FIG. 15.

The model selection unit 18 selects one or more related machine learning models related to the attribute of the occupant from a plurality of machine learning models (1 to N) 17 on the basis of the attribute information acquired in step ST1502 by the attribute-information acquisition unit 121 of the authentication unit 12*b* (step ST1504).

The model selection unit 18 outputs information of the selected one or more related machine learning models to the threshold setting unit 14*b* and the estimation unit 15*b*.

The control unit determines whether or not the related-model-specific threshold is set (step ST1505). Specifically, the control unit determines whether or not the related-model-specific threshold information corresponding to all the related machine learning models is stored in the storage unit.

Figure 16:
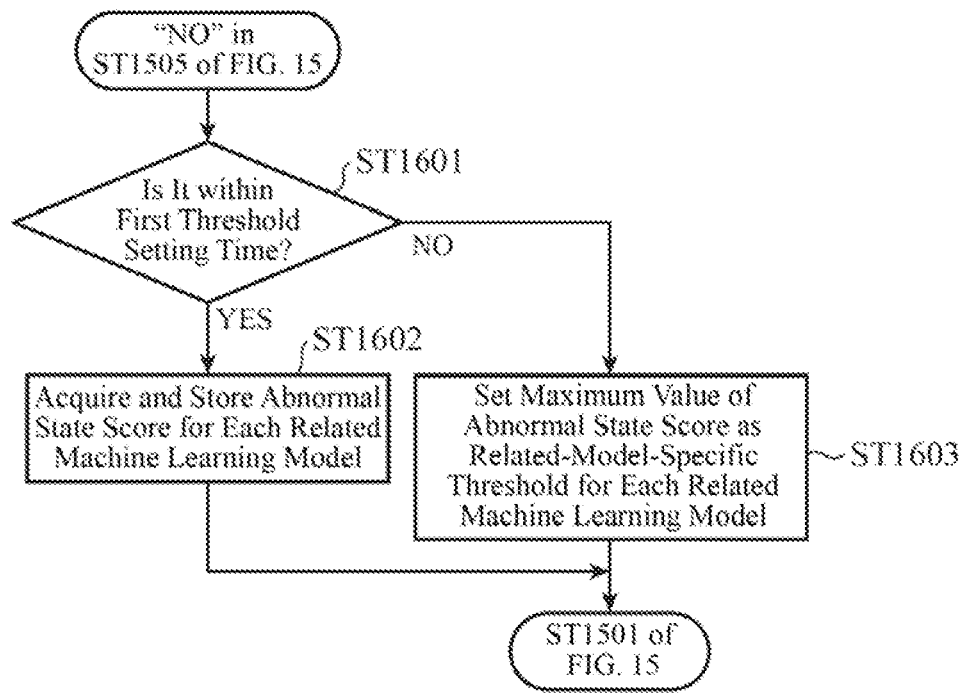
FIG. 16 is a flowchart for explaining a specific operation of step ST1506 in FIG. 15.

If it is determined in step ST1505 that the related-model-specific threshold is not set ("NO" in step ST1505), the operation of the flowchart FIG. 15 proceeds to step ST1506. Note that since the related-model-specific threshold is not set before the operation to be described later with reference to FIG. 16 is performed, the control unit determines that the related-model-specific threshold is not set. Since the related-model-specific threshold has been set after the operation to be described later with reference to FIG. 16 is performed, the control unit determines that the related-model-specific threshold is set.

The threshold setting unit 14*b* then performs "related-model-specific threshold setting process" (step ST1506).

Here, FIG. 16 is a flowchart for explaining a specific operation or step ST1506 in FIG. 15.

The related-model-specific threshold setting unit 143 determines whether or not it is within the first threshold setting time (step ST1601).

If the related-model-specific threshold setting unit 143 determines in step ST1601 that it is within the last threshold setting time ("YES" in step ST1601), the related-model-specific threshold setting unit 143 acquires the abnormal state score by inputting the feature amount most recently calculated in step ST1503 of FIG. 15 by the feature-amount calculation unit 13 to a certain related machine learning model of one or more related machine learning models. The related-model-specific threshold setting unit 143 performs the acquisition of the abnormal state score for all the related machine learning models as described above, and acquires the abnormal state score corresponding to each of the related machine learning models. The related-model-specific threshold setting unit 143 generates third score information and stores the third score information in the storage unit (step ST1602). Thereafter, the operation of the flowchart of FIG. 16 returns to step ST1501 of FIG. 15, and when the operation of step ST1501 is performed, the process proceeds to the operation of steps subsequent to stop ST1501 again. The related-model-specific threshold setting unit 143 performs the operation of step ST1602 thereafter until the first threshold setting time elapses ("NO" at step ST1601). As a result, the third score information generated within the first threshold setting time by the related-model-specific threshold setting unit 143 is stored in the storage unit.

If the related-model-specific threshold setting unit 143 determines in step ST1601 that it is not within the first threshold setting time, that is, if the first threshold setting time elapses ("NO" in step ST1601), the related-model-specific threshold setting unit 143 sets, with respect to a certain related machine learning model of one or more related machine learning models, the maximum value of one or more abnormal state scores stored in the storage unit within the first threshold setting time as the related-model-specific threshold (step ST1603). The related-model-specific threshold setting unit 143 performs the setting of the related-model-specific threshold for all the related machine learning models as described above, and sets the related-model-specific threshold corresponding to each of the related machine learning models. The related-model-specific threshold setting unit 143 generates related-model-specific threshold information, and stores the generated related-model-specific threshold information in the storage unit. Thereafter, the operation of the flowchart of FIG. 16 returns to step ST1501 of FIG. 15, and when the operation of step ST1501 is performed, the process proceeds to the operation of steps subsequent to step ST1501 again.

The description returns to the flowchart of FIG. 15.

If the control determines in step ST1505 that the related-model-specific threshold is set ("YES" in step ST1505), the operation of the flowchart in FIG. 15 proceeds to step ST1507.

In step ST1507, the control unit determines whether or not the abnormal-state determination threshold is set. Specifically, the control unit determines whether or not the estimatable flag "1" (step ST1507).

Figure 17:
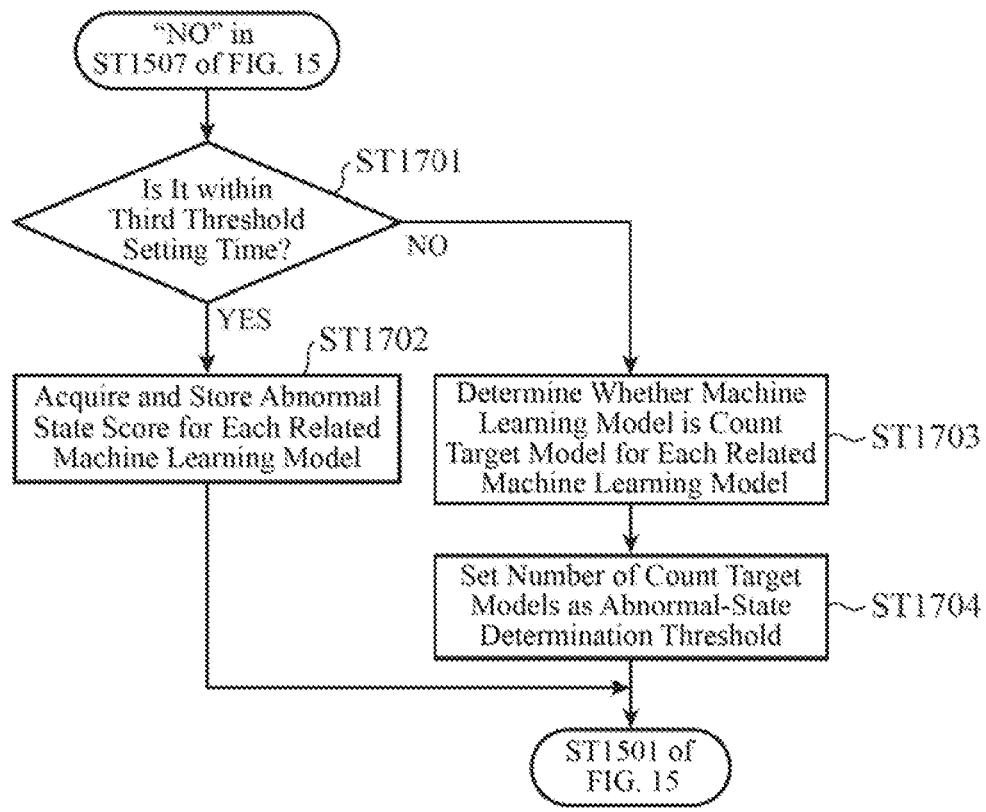
FIG. 17 is a flowchart for explaining a specific operation of step ST1508 in FIG. 15.

If the control unit determines in step ST1507 that the abnormal-state determination threshold is not set, in other words, if the control unit determines that the estimatable flag is "0" ("NO" in step ST1507), the operation of the flowchart of FIG. 15 proceeds to step ST1508. Note that since the abnormal-state determination threshold is not set before the operation to be described later with reference to FIG. 17 is performed, the control unit determines that the abnormal-state determination threshold is not set. Since the abnormal-state determination threshold has been set after the operation to be described later with reference to FIG. 17 is performed, the control unit determines that the abnormal-state determination threshold is set.

The threshold setting unit 14*b* then performs "abnormal-state determination threshold setting process" (step ST1508).

Here, FIG. 17 is a flowchart for explaining a specific operation of step ST1508 in FIG. 15.

The related-model-specific determination unit 144 of the threshold setting unit 14b determines whether or not it is within the third threshold setting time (step ST1701).

If the related-model-specific determination unit 144 determines in step ST1701 that it is within the third threshold setting time ("YES" in step ST1701), the related-model-specific determination unit 144 acquires the abnormal state score by inputting the feature amount most recently calculated in step ST1503 of FIG. 15 by the feature-amount calculation unit 13 to a certain related machine learning model of one or more related machine learning models. The related-model-specific determination unit 144 performs the acquisition of the abnormal state score for all the related machine learning models as described above, and acquires the abnormal state score corresponding to each of the related machine learning models. The related-model-specific determination unit 144 generates fourth score information and stores the fourth score information in the storage unit (step ST1702). Thereafter, the operation of the flowchart of FIG. 17 returns to step ST1501 of FIG. 15, and when the operation of step ST1501 is performed, the process proceeds to the operation of steps subsequent to step ST1501 again. The related-model-specific determination unit 144 performs the operation of step ST1702 thereafter until the third threshold setting time elapses ("NO" in step ST1701). As a result, the fourth score information generated within the third threshold setting time by the related-model-specific determination unit 144 is stored in the storage unit.

If the related-model-specific determination unit 144 determines in step ST1701 that it is not within the third threshold setting time, that is, if the third threshold setting time elapses ("NO" in step ST1701), the related-model-specific determination unit 144 determines whether or not any of one or more abnormal state scores of a certain related machine learning model of one or more related machine learning models, the abnormal state scores being stored in the storage unit within the third threshold setting time, is larger than the related-model-specific threshold set by the related-model-specific threshold setting unit 143.

In a case where at least one of one or more abnormal state scores obtained from the certain related machine learning model is larger than the related-model-specific threshold, the related-model-specific determination unit 144 determines the certain related machine learning model as the related machine learning model corresponding to the count target model (step ST1703). The related-model-specific determination unit 144 determines whether or not each of all the related machine learning models corresponds to "count target model".

The related-model-specific determination unit 144 generates related-model-specific count-necessity determination result information, and outputs the related-model-specific count-necessity determination result information to the threshold setting unit 14b.

The threshold setting unit 14b sets the number of count target models as the abnormal-state determination threshold on the basis of the related-model-specific count-necessity determination result information output from the related-model-specific determination unit 144 in step ST1703 (step ST1704).

The threshold setting unit 14b stores the set abnormal-state determination threshold in the storage unit in association with the personal identification information output from the authentication unit 12b, and sets the estimatable flag to "1". Thereafter, the operation of the flowchart of FIG. 17 returns to step ST1501 of FIG. 15, and when the operation of step ST1501 is performed, the process proceeds to the operation of steps subsequent to step ST1501 again.

The description returns to the flowchart of FIG. 15.

If the control unit determines in step ST1507 that the abnormal-state determination threshold is set, in other words, if the control unit determines that the estimatable flag is "1" ("YES" in step ST1507), the operation of the flowchart of FIG. 15 proceeds to step ST1509.

The estimation unit 15b then estimates the abnormal state of the occupation the basis of the abnormal state score obtained by inputting the feature amount related to the occupant calculated in step ST1503 by the feature-amount calculation unit 13 to each related machine learning model (step ST1509).

Figure 18:
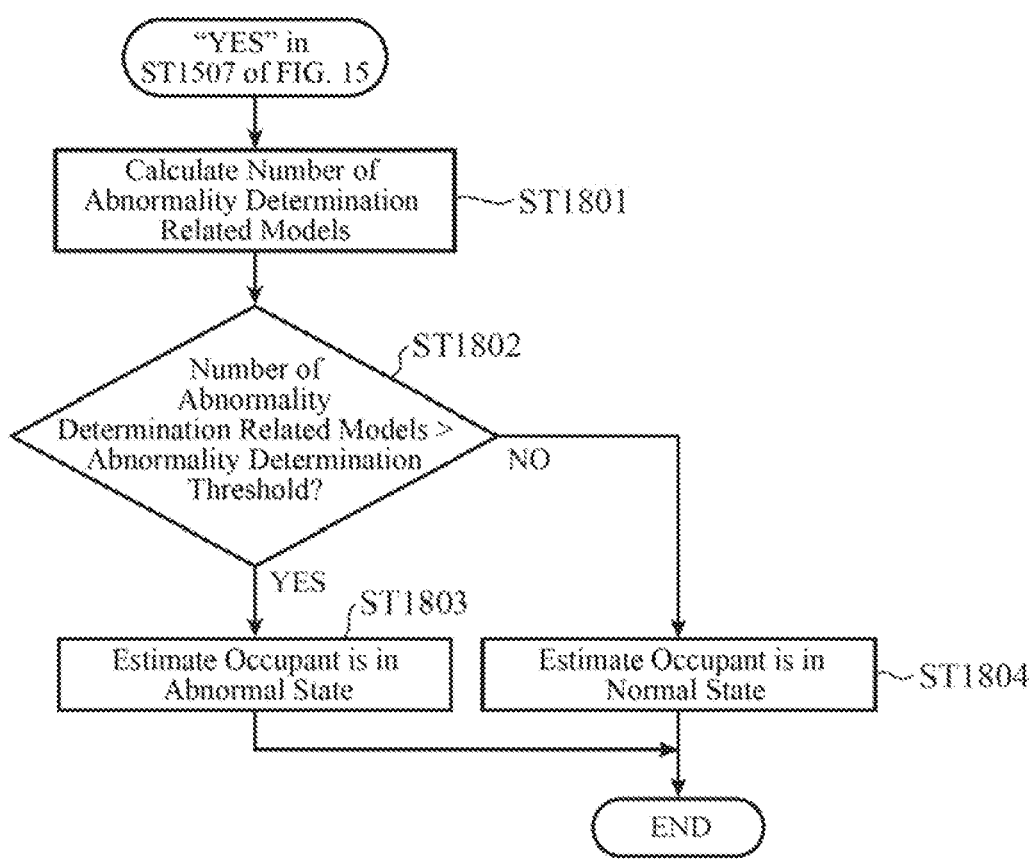
FIG. 18 is a flowchart for explaining a specific operation of step ST1509 in FIG. 15.

Here, FIG. 18 is a flowchart for explaining a specific operation of step ST1509 in FIG. 15.

The number-of-related-models calculation unit 152 of the estimation unit 15b first inputs the feature amount most recently calculated in step ST1503 of FIG. 15 by the feature-amount calculation unit 13 to a certain related machine learning model among one or more related machine learning models, and acquires the abnormal state score. The number-of-related-models calculation unit 152 then determines whether or not the acquired abnormal state score is larger than the related-model-specific threshold set in step ST1603 of FIG. 16 by the related-model-specific threshold setting unit 143.

The number-of-related-models calculation unit 152 determines whether or not the abnormal state score is larger than the related-model-specific threshold for all the related machine learning models. The number-of-related-models calculation unit 152 then calculates the number of abnormality determination related models (step ST1801).

The number-of-related-models calculation unit 152 outputs the calculated number of abnormality determination related models to the estimation unit 15b.

The estimation unit 15b compares the number of abnormality determination related models calculated in step ST1801 by the number-of-related-models calculation unit 152 with the abnormal-state determination threshold set in step ST1704 of FIG. 17 by the threshold setting unit 14b (step ST1802).

If it is determined in step ST1802 that the number of abnormality determination related models is larger than the abnormal-state determination threshold ("YES" in step ST1802), the estimation unit 15b determines that the occupant is in the abnormal state (step ST1803).

On the other hand, if it is determined in step ST1802 that the number of abnormality determination related models is less than or equal to the abnormal-state determination threshold ("NO" in step ST1802), the estimation unit 15b determines that the occupant is in the normal state (step ST1804).

Note that in the above description of the operation, the threshold setting unit 14b performs the operation described in the flowchart of FIG. 17 and sets the abnormal-state determination threshold in "abnormal-state determination threshold setting process". However, this is merely an example. For example, the threshold setting unit 14b may set the abnormal-state determination threshold by performing an operation as described below.

In a case where it is within the third threshold setting time, the related-model-specific determination unit 144 of the threshold setting unit 14b inputs the feature amount most recently calculated in step ST1503 of FIG. 15 by the feature-amount calculation unit 13 to a certain related machine learning model among one or more related machine learning models, and acquires the abnormal state score. Subsequently, the related-model-specific determination unit 144 determines whether or not the certain related machine learning model corresponds to a "count target model" by determining whether or not the acquired abnormal state score is larger than the related-model-specific threshold set in step ST1603 of FIG. 16 by the related-model-specific threshold setting unit 143. In a case where the abnormal state score obtained from the certain related machine learning model is larger than the related-model-specific threshold set by the related-model-specific threshold setting unit 143, the related-model-specific determination unit 144 determines that the certain related machine learning model corresponds to the "count target model".

The related-model-specific determination unit 144 acquires the abnormal state score and determines whether or not the related machine learning model corresponds to the count target model for all the related machine learning models. The related-model-specific determination unit 144 acquires the abnormal state score and determines whether or not the related machine learning model correspond to the count target model for all the related machine learning models, and then calculates the number of related machine learning models corresponding to the count target model among all the related machine learning models. The related-model-specific determination unit 144 stores the calculated number of count target models in the storage unit in association with, for example, the time when the number is calculated.

The related-model-specific determination unit 144 performs the above operation for the third threshold setting time every time the feature-amount calculation unit 13 calculates the feature amount.

When the third threshold setting time elapses, the threshold setting unit 14$b$ sets the maximum value of the number of count target models calculated by the related-model-specific determination unit 144 within the third threshold setting time as the abnormal-state determination threshold. At this time, the threshold setting unit 14$b$ may set the abnormal-state determination threshold by providing a buffer to the maximum value of the number of count target models calculated within the third threshold setting time. Specifically, the threshold setting unit 14$b$ may set the maximum value of the number of count target models calculated within the third threshold setting time+$\alpha$ as the abnormal-state determination threshold. $\alpha$ is assumed to be larger than 0.

As described above, the driver availability detection device 1$b$ according to the third embodiment selects one or more related machine learning models related to the attribute of the occupant from the machine learning models (1 to N) 17. The driver availability detection device 1$b$ assumes that the occupant is in the normal state for the first threshold setting time, and sets, for each related machine learning model, the related-model-specific threshold on the basis of the maximum value of the abnormal state score obtained by inputting the feature amount related to the occupant during the first threshold setting time.

Further, after setting the related-model-specific threshold, the driver availability detection device 1$b$ assumes that the occupant is in the normal state for the third threshold setting time, compares the abnormal state score obtained by inputting the feature amount related to the occupant during the third threshold setting time with the related-model-specific threshold for each related machine learning model, and calculates the number of related machine learning models corresponding to the count target model among the related machine learning models. The driver availability detection device 1$b$ then sets the calculated number of count target models as the abnormal-state determination threshold.

After setting the abnormal-state determination threshold, the driver availability detection device 1$b$ inputs the feature amount related to the occupant for each related machine learning model and acquires the abnormal state score for each related machine learning model. The driver availability detection device 1$b$ determines, for each related machine learning model, whether or not the obtained abnormal state score is larger than the related-model-specific threshold. The driver availability detection device 1$b$ then calculates the number of abnormality determination related models.

After calculating the number of abnormality determination related models, the driver availability detection device 1$b$ compares the number of abnormality determination related models with the abnormal-state determination threshold, and estimates that the occupant is in the abnormal state in a case where the number of abnormality determination related models is larger than the abnormal-state determination threshold.

The driver availability detection device 1$b$ does not estimate whether or not the occupant is in the abnormal state using a fixed threshold, but sets the abnormal-state determination threshold for each occupant, and estimates whether or not the occupant is in the abnormal state using the abnormal-state determination threshold. Consequently, when estimating whether or not the occupant is in the abnormal state, the driver availability detection device 1$b$ can prevent erroneous estimation of the abnormal state of the occupant.

In addition, the driver availability detection device 1$b$ sets the abnormal-state determination threshold and estimates the abnormal state of the occupant on the basis of a related machine learning model among a plurality of machine learning models individually generated in advance depending on attributes of a plurality of occupants with various attributes. As a result, the driver availability detection device 1$b$ can improve the accuracy of estimating the abnormal state of the occupant as compared with the case of setting the abnormal-state determination threshold and estimating the abnormal state of the occupant using all the machine learning models generated from the information related to the occupants with various attributes.

Note that also in the driver availability detection device 1$b$ according to the third embodiment like the driver availability detection device 1 according to the first embodiment, for example, the estimation unit 15$b$ may estimate that the occupant is in the abnormal state when the rate at which the occupant is estimated to be in the abnormal state is larger than or equal to a threshold during the driver availability detection time, and thereafter, does not have to estimate the abnormal state of the occupant until the driving of the vehicle is ended.

According to the third embodiment, in the driver availability detection device 1$b$, the information input to the related machine learning model is the feature amount related to the occupant calculated by the feature-amount calculation unit 13, but this is merely an example. For example, in the driver availability detection device 1$b$, the information input to the related machine learning model may be information related to the occupant acquired by the information acquisition unit 11. In this case, the driver detection device 1$b$ can be configured not to include the feature-amount calculation unit 13.

Note, however, that when the driver availability detection device 1$b$ includes the feature-amount calculation unit 13 and inputs the feature amount related to the occupant, the feature amount having a large correlation with the estimation of the abnormal state, to the related machine learning model, the accuracy of estimation at the time of estimating the abnormal state of the occupant can be improved as compared with the case where the information related to the occupant is directly input to the related machine learning model.

Note that, in a case where the information input to the related machine learning model is the information related to the occupant in the driver availability detection device 1b, the learning device sets the information related to the occupant as teacher data.

As described above, according to the third embodiment, the driver availability detection device 1b that estimates the abnormal state of the occupant on the basis or the information related to the occupant of the vehicle and the related machine learning model (1 to N) 17 includes the information acquisition unit 11 that acquires the information related to the occupant and the threshold setting unit 14b that sets the abnormal-state determination threshold for estimating the abnormal state of the occupant on the basis of the abnormal state score obtained by inputting the information related to the occupant acquired by the information acquisition unit to the machine learning model (1 to N) 17 within the first threshold setting time.

Consequently, when estimating whether or not the occupant is in the abnormal state, the driver availability detection device 1b can prevent erroneous estimation of the abnormal state of the occupant.

In particular, in the third embodiment, there is a plurality of machine learning models (1 to N) 17, and the driver availability detection device 1b includes the attribute-information acquisition unit 121 that acquires the attribute information related to the attribute of the occupant, the model selection unit 18 that selects one or more related machine learning models related to the attribute of the occupant among the machine learning models (1 to N) 17 on the basis of the attribute information acquired by the attribute-information acquisition unit 121, the related-model-specific threshold setting unit 143 that sets, for each of one or more related machine learning models selected by the model selection unit 18, the related-model-specific threshold on the basis of the abnormal state score obtained by inputting the information related to the occupant acquired by the information acquisition unit 11 within the first threshold setting time, and the related-model-specific determination unit 144 that determines, after the related-model-specific threshold setting unit 143 sets the related-model-specific threshold, whether or not the abnormal state score obtained by inputting the information related to the occupant acquired by the information acquisition unit 11 within the third threshold setting time is larger than the related-model-specific threshold set by the related-model-specific threshold setting unit 143 for each of one or more related machine learning models, and the threshold setting unit 14b sets the number of related machine learning models in which the related-model-specific determination unit 144 determines that the abnormal state score is larger than the related-model-specific threshold as the abnormal-state determination threshold.

As a result, the driver availability detection device 1b can further improve the accuracy of estimating the abnormal state of the occupant as compared with the case of setting the abnormal-state determination threshold and estimating the abnormal state of the occupant using all of a plurality of machine learning models generated from the information related to the occupants with various attributes.

In the first to third embodiments, it is assumed that the occupant of the vehicle is a driver, and the driver availability detection devices 1 to 1b estimate whether or not the driver is in the abnormal state. However, this is merely an example.

In the first to third embodiments, the occupant of the vehicle may be, for example, a passenger seated on a passenger seat or a rear seat. In this case, the abnormal state of the occupant estimated by the driver availability detection devices 1 to 1b means a state where the occupant is in poor physical condition. Specifically, the abnormal state of the occupant means, for example, a state where the occupant is drunk or a state where the occupant is tired. Furthermore, in this case, the start of driving of the vehicle means, for example, when the driver starts to drive the vehicle.

Further, according to the first to third embodiments described above, in the driver availability detection devices 1 to 1b, the information acquisition unit 11 acquires the facial image, the biological information, and the vehicle information, but this is merely an example. The information acquisition unit 11 is only required to acquire at least one of the facial image, the biological information, or the vehicle information as the information related to the occupant. The feature-amount calculation unit 13 calculates the feature amount related to the occupant on the basis of the information related to the occupant acquired by the information acquisition unit 11.

Furthermore, in the first to third embodiments described above, the estimation result of whether or not the occupant is in the abnormal state estimated by the driver availability detection devices 1 to 1b is used in various scenes.

For example, it is assumed that the vehicle on which the driver availability detection devices 1 to 1b are mounted is an autonomous driving vehicle, and the driver availability detection devices 1 to 1b estimate whether or not the driver is in the abnormal state. In this case, for example, when the driver availability detection devices 1 to 1b estimate that the driver in the abnormal state, the driver availability detection devices 1 to 1b output an estimation result indicating that the driver is in the abnormal state to an autonomous driving control unit (not illustrated) mounted on the vehicle. When the estimation result indicating that the driver is in the abnormal state is output from the driver availability detection devices 1 to 1b, the autonomous driving control unit executes control to apply an automatic brake at early timing. Further, for example, when the driver availability detection devices 1 to 1b output the estimation result that the driver is in the abnormal state, the autonomous driving control unit prohibits switching to manual driving and executes control to move the vehicle to a shoulder of a road.

Furthermore, for example, it is assumed that the driver availability detection devices 1 to 1b estimate an abnormal state of a passenger. In this case, for example, when the driver availability detection devices 1 to 1b estimate that the passenger is in the abnormal state, the driver availability detection devices 1 to 1b output an estimation result indicating that the passenger is in the abnormal state to a communication device (not illustrated) outside the driver availability detection devices 1 to 1b. When the estimation result indicating that the passenger is in the abnormal state is output from the driver availability detection devices 1 to 1b, the communication device reports to an emergency center.

Figure 19A:
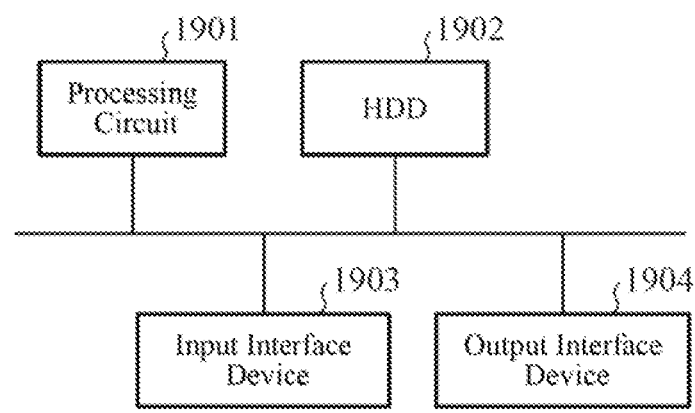
FIGS. 19A and 19B are diagrams illustrating an example of a hardware configuration of the driver availability detection devices 1 to 1$b$ according to the first to third embodiments.
Figure 19B:
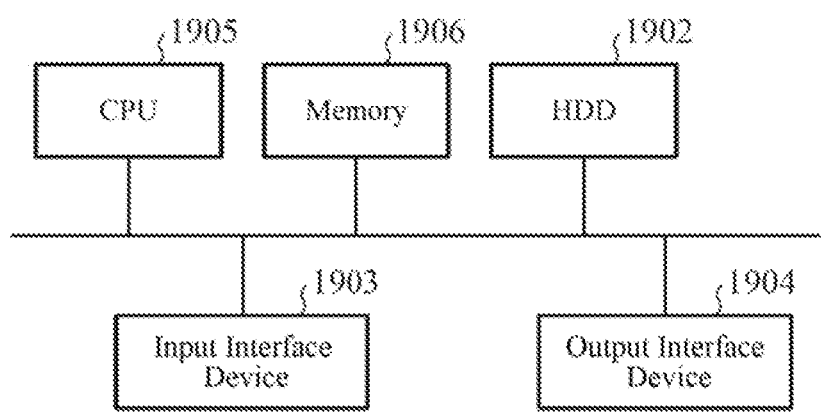

FIGS. 19A and 19B are diagrams illustrating an example of a hardware configuration of the driver availability detection devices 1 to 1b according to the first to third embodiments.

In the first to third embodiments, the functions of the information acquisition unit 11, the authentication units 12 and 12b, the feature-amount calculation unit 13, the threshold setting units 14, 14a, and 14b, the estimation units 15, 15a, and 15b, and the model selection unit 18 are implemented by a processing circuit 1901. That is, the driver availability detection devices 1 to 1b include the processing circuit 1901 for controlling the setting of an abnormal-state determination threshold used for estimating the abnormal state of an occupant of a vehicle.

The processing circuit 1901 may be dedicated hardware as illustrated in FIG. 19A, or may be a central processing unit (CPU) 1905 that executes a program stored in a memory 1906 as illustrated in FIG. 19B.

In a case where the processing circuit 1901 is dedicated hardware, the processing circuit 1901 corresponds to, for example, a single circuit, a composite circuit, a programmed processor, a parallel programmed processor, an application specific integrated circuit (ASIC), a field-programmable gate array (FPGA), or a combination thereof.

In a case whet the processing circuit 1901 is the CPU 1905, the functions of the information acquisition unit 11, the authentication units 12 and 12b, the feature-amount calculation unit 13, the threshold setting units 14, 14a, and 14b, the estimation units 15, 15a, and 15b, and the model selection unit 18 are implemented by software, firmware, or a combination of software and firmware. That is, the information acquisition unit 11, the authentication units 12 and 12b, the feature-amount calculation unit 13, the threshold setting units 14, 14a, and 14b, the estimation units 15, 15a, and 15b, and the model selection unit 18 are implemented by a processing circuit such as the CPU 1905 that executes a program stored in a hard disk drive (HDD) 1902, a memory 1906, or the like, or a system large-scale integration (LSI). It can also be said that the programs stored in the HDD 1902, the memory 1906, and the like cause a computer to perform the procedures or methods performed by the information acquisition unit 11, the authentication units 12 and 12b, the feature-amount calculation unit 13, the threshold setting units 14, 14a, and 14b, the estimation units 15, 15a, and 15b, and the model selection unit 18. Here, the memory 1906 corresponds to, for example, a nonvolatile or volatile semiconductor memory such as a RAM, a read only memory (ROM), a flash memory, an erasable programmable read only memory (EPROM), or an electrically erasable programmable read only memory (EEPROM), a magnetic disk, a flexible disk, an optical disk, a compact disk, a mini disk, a digital versatile disc (DVD), or the like.

Note that a part of the functions of the information acquisition unit 11, the authentication units 12 and 12b, the feature-amount calculation unit 13, the threshold setting units 14, 14a, and 14b, the estimation units 15, 15a, and 15b, and the model selection unit 18 may be implemented by dedicated hardware, and a part thereof may be implemented by software or firmware. For example, the functions of the authentication units 12 and 12b can be implemented by the processing circuit 1901 as dedicated hardware, and the functions of the information acquisition unit 11, the feature-amount calculation unit 13, the threshold setting units 14, 14a, and 14b, the estimation units 15, 15a, and 15b, and the model selection unit 18 can be implemented by the processing circuit 1901 reading and executing a program stored in the memory 1906.

In addition, the personal authentication DB 16 and a storage unit (not illustrated) use the memory 1906. Note that this is an example, and the personal authentication DB 16 and a storage unit (not illustrated) may be configured by the HDD 1902, a solid state drive (SSD), a DVD, or the like.

Furthermore, the driver availability detection devices 1 to 1b include an input interface device 1903 and an output interface device 1904 that perform wired communication or wireless communication with a device such as the image capturing device 2 or the biometric sensor 3.

Note that, in the first to third embodiments described above, the driver availability detection devices 1 to 1b are an in-vehicle device mounted on a vehicle, and the information acquisition unit 11, the authentication units 12 and 12b, the feature-amount calculation unit 13, the threshold setting units 14, 14a, and 14b, the estimation units 15, 15a, and 15b, and the model selection unit 18 are included in the driver availability detection devices 1 to 1b.

No limitation is intended thereto, and a part of the information acquisition unit 11, the authentication units 12 and 12b, the feature-amount calculation unit 13, the threshold setting units 14, 14a and 14b, the estimation units 15, 15a and 15b, and the model selection unit 18 may be mounted on the in-vehicle device of the vehicle, and the remaining part may be provided in a server connected to the in-vehicle device via a network, so that the in-vehicle device and the server may constitute a driver availability detection system.

In addition, in the present invention, it is possible to freely combine the embodiments, modify any component of each embodiment, or omit any component in each embodiment within the scope of the invention.

INDUSTRIAL APPLICABILITY

The driver availability detection device according to the present invention can be applied to a driver availability detection device that estimates whether or not an occupant of a vehicle is in an abnormal state on the basis of information related to the occupant and a machine learning model.

REFERENCE SIGNS LIST 1, 1a, and 1b: driver availability detection device, 2: image capturing device, 3: biometric sensor, 11: information acquisition unit, 111: facial-image acquisition unit, 1111: face detection unit, 112: biological-information acquisition unit, 113: vehicle-information acquisition unit, 12, and 12b: authentication unit, 13: feature-amount calculation unit, 131: facial feature-amount calculation unit, 132: biological feature-amount calculation unit, 133: vehicle operation feature-amount calculation unit, 14, 14a, and 14b: threshold setting unit, 141: model-specific threshold setting unit, 142: model-specific determination unit, 143: related-model-specific threshold setting unit, 144: related-model-specific determination unit, 15, 15a, and 15b: estimation unit, 151: number-of-models calculation unit, 152: number-of-related-models calculation unit, 16: personal authentication DB, 17: machine learning model, 1901: processing circuit, 1902: HDD, 1903: input interface device, 1904: output interface device, 1905; CPU, 1906: memory

The invention claimed is:

1. A driver availability detection device using a machine learning model, the driver availability detection device comprising:

processing circuitry to acquire information related to the occupant, to set an abnormal-state determination threshold that is adapted for the occupant, on a basis of an abnormal state score obtained by inputting information related to the occupant to the machine learning model that is trained using facial features, vehicle operational features, and biological features of a plurality of test occupants, within a first threshold setting time, and to estimate an abnormal state of the occupant based on the abnormal-state determination threshold that is adapted for the occupant.

2. The driver availability detection device according to claim 1, wherein the processing circuitry obtains one or more abnormal state scores and sets a maximum value of the one or more abnormal state scores as the abnormal-state determination threshold.

3. The driver availability detection device according to claim 1, wherein the processing circuitry estimates that the occupant is in an abnormal state in a case where the abnormal state score obtained by inputting the information related to the occupant to the machine learning model is larger than the abnormal-state determination threshold.

4. The driver availability detection device according to claim 3, wherein the processing circuitry individually authenticates the occupant and acquire personal identification information for identifying the occupant, stores the abnormal-state determination threshold, which has been set, in association with the personal identification information, and estimates the abnormal state of the occupant when acquiring the personal identification information and storing the abnormal-state determination threshold in association with the personal identification information.

5. The driver availability detection device according to claim 1, wherein there are a plurality of the machine learning models, the processing circuitry sets a model-specific threshold for each of the machine learning models on a basis of an abnormal state score obtained by the inputting information related to the occupant within the first threshold setting time, and determines, after setting the model-specific threshold, whether or not an abnormal state score obtained by inputting information related to the occupant within a second threshold setting time is larger than the model-specific threshold for each of the machine learning models, and sets a number of the machine learning models in which it is determined that the abnormal state score is larger than the model-specific threshold as the abnormal-state determination threshold.

6. The driver availability detection device according to claim 5, wherein the processing circuitry calculates a number of machine learning models in which an abnormal state score obtained by inputting information related to the occupant is larger than a model-specific threshold, among the machine learning models, and estimates that the occupant is in the abnormal state in a case where the number of the machine learning models is larger than the abnormal-state determination threshold.

7. The driver availability detection device according to claim 1, wherein the processing circuitry acquires attribute information related to an attribute of the occupant, selects one or more related machine learning models related to the attribute of the occupant among the machine learning models on a basis of the attribute information, sets, for each of the one or more related machine learning models, a related-model-specific threshold on a basis of an abnormal state score obtained by inputting information related to the occupant within the first threshold setting time, determines, after setting the related-model-specific threshold, whether or not an abnormal state score obtained by inputting information related to the occupant within a third threshold setting time is larger than the related-model-specific threshold for each of the one or more related machine learning models, and sets a number of the related machine learning models in which it is determined that the abnormal state score is larger than the related-model-specific threshold as the abnormal-state determination threshold.

8. The driver availability detection device according to claim 7, wherein the attribute of the occupant is an age of the occupant.

9. The driver availability detection device according to claim 7, wherein the processing circuitry counts a number of related machine learning models in which an abnormal state score obtained by inputting information related to the occupant to the related machine learning model is larger than a related-model-specific threshold, among the machine learning models, and estimates that the occupant is in an abnormal state in a case where the number of the related machine learning models is larger than the abnormal-state determination.

10. The driver availability detection device according to claim 1, wherein the processing circuitry calculates a feature amount related to the occupant on a basis of information related to the occupant, and sets the abnormal-state determination threshold on a basis of an abnormal state score obtained by inputting the feature amount to the machine learning model within the first threshold setting time.

11. A driver availability detection method using a machine learning model, the driver availability detection method comprising:

acquiring information related to the occupant; and setting an abnormal-state determination threshold that is adapted for the occupant, on a basis of an abnormal state score obtained by inputting information related to the occupant to the machine learning model that is trained using facial features, vehicle operational features, and biological features of a plurality of test occupants, within a first threshold setting time; and estimating an abnormal state of the occupant based on the abnormal-state determination threshold that is adapted for the occupant.

\* \* \* \* \*